United States Patent
Ise et al.

(10) Patent No.: US 10,428,268 B2
(45) Date of Patent: Oct. 1, 2019

(54) ORGANIC ELECTROLUMINESCENCE ELEMENT

(75) Inventors: Toshihiro Ise, Kanagawa (JP); Tetsu Kitamura, Kanagawa (JP); Toru Watanabe, Kanagawa (JP)

(73) Assignee: UDC Ireland Limited, Dublin (IE)

(*) Notice: Subject to any disclaimer, the term of this patent is extended or adjusted under 35 U.S.C. 154(b) by 825 days.

(21) Appl. No.: 13/522,126

(22) PCT Filed: Dec. 28, 2010

(86) PCT No.: PCT/JP2010/073821
§ 371 (c)(1),
(2), (4) Date: Jul. 13, 2012

(87) PCT Pub. No.: WO2011/086866
PCT Pub. Date: Jul. 21, 2011

(65) Prior Publication Data
US 2012/0292608 A1 Nov. 22, 2012

(30) Foreign Application Priority Data
Jan. 15, 2010 (JP) ................... 2010-007540

(51) Int. Cl.
*H01L 51/50* (2006.01)
*C09K 11/06* (2006.01)
(Continued)

(52) U.S. Cl.
CPC .......... *C09K 11/06* (2013.01); *H01L 51/0058* (2013.01); *H01L 51/0085* (2013.01);
(Continued)

(58) Field of Classification Search
CPC ............ H01L 51/0058; H01L 51/0085; H01L 51/0037; H01L 51/0059; H01L 51/006;
(Continued)

(56) References Cited

U.S. PATENT DOCUMENTS 9,112,171 B2 * 8/2015 D'Andrade ............ C07C 15/28
9,296,944 B2 * 3/2016 Ise ........................ C09K 11/06
(Continued)

FOREIGN PATENT DOCUMENTS

JP 2005220136 A 8/2005
JP 2009099783 A 5/2009
(Continued)

OTHER PUBLICATIONS

International Search Report dated Mar. 29, 2011 issued in International Application No. PCT/JP2010/073821 (PCT/ISA/210).
(Continued)

Primary Examiner — Andrew K Bohaty
Assistant Examiner — Dylan C Kershner
(74) Attorney, Agent, or Firm — Riverside Law LLP

(57) ABSTRACT

A light emitting organic thin film including at least one compound represented by Formula (PQ-1) and at least one compound represented by Formula (BN-1).

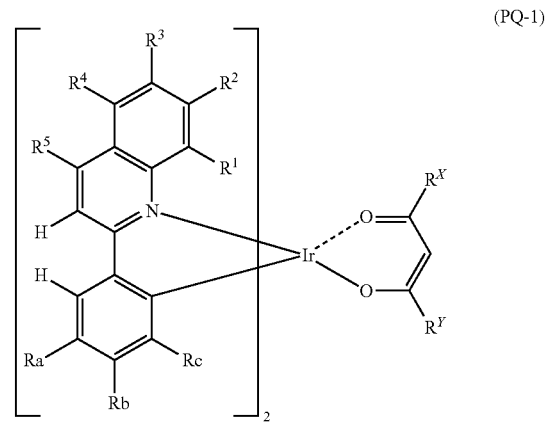

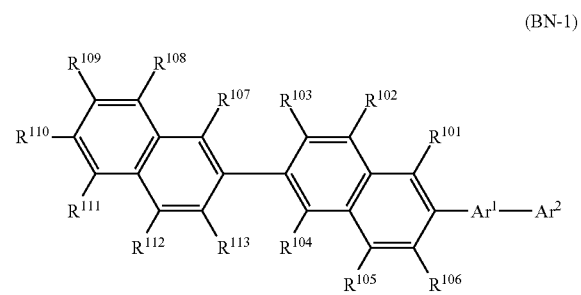

In Formula (PQ-1), each of $R^a$, $R^b$ and $R^c$ independently represents a hydrogen atom or an alkyl group, wherein any one of $R^a$, $R^b$ and $R^c$ represents a hydrogen atom and the remaining two represent an alkyl group. Each of $R^1$ to $R^5$ independently represents a hydrogen atom, an alkyl group, an aryl group, a fluorine atom or a cyano group. Each of $R^x$ and $R^y$ independently represents an alkyl group or a phenyl group. In Formula (BN-1), $Ar^1$ represents an arylene group that may have a substituent Z. $Ar^2$ represents a condensed hydrocarbyl group that may have a substituent Z. Each of $R^{101}$ to $R^{113}$ independently represents a phenyl group, or the like.

13 Claims, 3 Drawing Sheets

(51) Int. Cl.
  *H01L 51/00* (2006.01)
  *H05B 33/14* (2006.01)
  *C07F 15/00* (2006.01)

(52) U.S. Cl.
  CPC .......... *H05B 33/14* (2013.01); *C07F 15/0033* (2013.01); *C09K 2211/1029* (2013.01); *C09K 2211/185* (2013.01); *H01L 51/006* (2013.01); *H01L 51/0037* (2013.01); *H01L 51/0059* (2013.01); *H01L 51/0072* (2013.01); *H01L 51/0081* (2013.01); *H01L 51/5016* (2013.01)

(58) Field of Classification Search
  CPC ............. H01L 51/0072; H01L 51/0081; H01L 51/5016; C09K 11/06; C09K 2211/1029; C07F 15/0033
  USPC ................. 428/690, 917, 691; 313/500–512; 427/58, 66; 257/40, 88–104, 257/E51.001–E51.052; 252/301.16–301.35
  See application file for complete search history.

(56) References Cited

U.S. PATENT DOCUMENTS

| | | | |
|---|---|---|---|
| 2004/0263065 A1* | 12/2004 | Yeh ...................... | H01L 27/322 313/504 |
| 2005/0127827 A1* | 6/2005 | Hiraoka et al. ............... | 313/504 |
| 2005/0170209 A1 | 8/2005 | Lee et al. | |
| 2006/0032528 A1* | 2/2006 | Wang ........................... | 136/263 |
| 2006/0186791 A1* | 8/2006 | Yoshitake et al. ............ | 313/503 |
| 2007/0057264 A1* | 3/2007 | Matsuda ............. | H01L 27/3211 257/88 |
| 2007/0088185 A1* | 4/2007 | Kubota ................. | C07C 13/567 585/407 |
| 2008/0261076 A1* | 10/2008 | Kwong et al. ................. | 428/690 |
| 2009/0008605 A1 | 1/2009 | Kawamura et al. | |
| 2009/0008606 A1 | 1/2009 | Kawamura et al. | |
| 2009/0008607 A1 | 1/2009 | Kawamura et al. | |
| 2009/0039317 A1 | 2/2009 | Kawamura et al. | |
| 2009/0045731 A1* | 2/2009 | Nishimura et al. ........... | 313/504 |
| 2009/0078317 A1 | 3/2009 | Kim et al. | |
| 2009/0085476 A1* | 4/2009 | Park et al. ..................... | 313/504 |
| 2009/0273278 A1 | 11/2009 | Lee et al. | |
| 2010/0001262 A1* | 1/2010 | Kim ........................ | C07C 15/28 257/40 |
| 2010/0096982 A1 | 4/2010 | Eum et al. | |
| 2010/0283043 A1* | 11/2010 | Nishimura et al. ............. | 257/40 |
| 2011/0001130 A1 | 1/2011 | Nishimura et al. | |
| 2011/0248250 A1 | 10/2011 | D'Andrade et al. | |

FOREIGN PATENT DOCUMENTS

| | | | |
|---|---|---|---|
| JP | 2009132706 | | 6/2009 |
| JP | 2009-147324 | | 7/2009 |
| JP | 2009218547 | A | 9/2009 |
| JP | 2009292807 | A | 12/2009 |
| JP | 201059158 | A | 3/2010 |
| JP | 2010520882 | | 6/2010 |
| JP | 2012506632 | A | 3/2012 |
| WO | 2009008198 | A1 | 1/2009 |
| WO | 2009008311 | A1 | 1/2009 |
| WO | 2009066778 | A1 | 5/2009 |
| WO | 2009066779 | A1 | 5/2009 |
| WO | WO 2009066779 | A1 * | 5/2009 |
| WO | WO 2010028151 | A1 * | 3/2010 .......... C07F 15/0033 |
| WO | 2010047707 | A1 | 4/2010 |

OTHER PUBLICATIONS

Written Opinion dated Mar. 29, 2011 issued International Application No. PCT/JP2010/073821 (PCT/ISA/237).
Japanese Office Action dated Jul. 27, 2012 issued by the Japanese Patent Office in counterpart Japanese Patent Application No. 2010-007540.
Japanese Office Action dated Jan. 17, 2012 issued by the Japanese Patent Office in counterpart Japanese Patent Application No. 2010-007540.

* cited by examiner

ORGANIC ELECTROLUMINESCENCE ELEMENT

TECHNICAL FIELD

The present invention relates to an organic electroluminescence device (hereinafter, referred to as "device" or "organic EL device"), as well as to a display apparatus and illumination apparatus using the same. Particularly, the present invention relates to development of a device that is excellent from the viewpoints of efficiency, durability and electric power consumption, and shows a small variation in characteristics depending on temperature of usage environment.

BACKGROUND ART

Since organic electroluminescence devices are capable of obtaining a light emission with high luminance intensity by low-voltage driving, the devices have been actively researched and developed. In general, organic electroluminescence devices have an organic layer including a light emitting layer and a pair of electrodes with the organic layer interposed therebetween, and utilize, for light emission, energy of the exciton generated as a result of recombination of electrons injected from a cathode and holes injected from an anode in the light emitting layer.

Improvement in the efficiency of devices has been recently made by using a phosphorescence emitting material. As a phosphorescence emitting material, iridium complexes, platinum complexes and the like are known (see, for example, Patent Document 1).

In addition, doped devices using a light emitting layer including a host material doped with a light emitting material have been utilized widely. Development of host materials has been conducted actively and an invention using an aromatic polycyclic condensed ring-based material as a host material has been known (see Patent Document 2, for example). Further, with regard to a phosphorescent material, an invention related to a light emitting spectrum with high color purity obtained by introducing a substituent to a specific position has been known (see Patent Document 3).

Devices have insufficient external quantum efficiency and durability, and require further improvement in their characteristics. Moreover, an increment in driving voltage caused by temperature of usage environment becomes an additional problematic obstacle in practice, and an improvement in such a problem is needed.

Patent Document 2 discloses use of a chrysene derivative as a host material for the purpose of fabrication of a device with high efficiency and long service life. In addition, Patent Document 3 discloses use of Ir complexes of phenylquinoline-based ligands having a substituent at a specific position in a high-performance red phosphorescence device. Further, Patent Document 4 discloses an embodiment in which a chrysene derivative is used as a host material for Ir complexes of specific phenylquinoline-based ligands, but no studies have been conducted about a difference in driving voltage increment upon driving under different driving environments, and thus, such an embodiment is highly problematic in practice.

RELATED ART

Patent Document

Patent Document 1: Japanese Patent Application Laid-Open No. 2005-220136

Patent Document 2: International Publication No. WO09/008311

Patent Document 3: US Patent Application No. 2008/0261076

Patent Document 4: Japanese Patent Application Laid-Open No. 2009-99783

DISCLOSURE OF INVENTION

Problems to be Solved by the Invention

In the devices according to the related art, a difference in driving voltage increment at different driving temperatures causes a severe problem, and thus, an improvement is needed.

The present inventors have found out that, when the host material including a chrysene structure according to the present invention is combined with a specific iridium complex material, high efficiency, low driving voltage or an effect of improving durability are realized, and simultaneously, dependency of an increment in post-driving voltage on temperature of usage environment is low.

Therefore, an object of the present invention is to provide an organic electroluminescence device which has high external quantum efficiency, low driving voltage and excellent durability, and to provide an organic electroluminescence device which shows low dependency of an increment in post-driving voltage on temperature of usage environment.

Another object of the present invention is to provide a composition, a light emitting organic thin film and a light emitting layer for use in an organic electroluminescence device. Moreover, still another object of the present invention is to provide a method for forming a film of a compound useful for an organic electroluminescence device. Yet another object of the present invention is to provide a light emission apparatus and an illumination apparatus, including the organic electroluminescence device.

Means for Solving the Problems

That is, the present invention was accomplished by the following means.

[1] A light emitting organic thin film including at least one compound represented by Formula (PQ-1) and at least one compound represented by Formula (BN-1).

[Chem. 1]

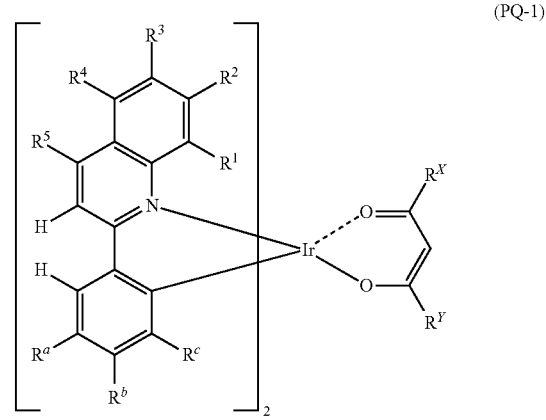

(PQ-1)

-continued (BN-1)

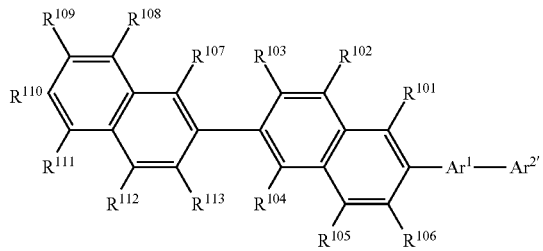

(In Formula (PQ-1), each of $R^a$, $R^b$ and $R^c$ independently represents a hydrogen atom or an alkyl group, wherein any one of $R^a$, $R^b$ and $R^c$ represents a hydrogen atom and the remaining two represent an alkyl group. Each of $R^1$ to $R^5$ independently represents a hydrogen atom, an alkyl group, an aryl group, a fluorine atom or a cyano group. Each of $R^x$ and $R^y$ independently represents an alkyl group or a phenyl group.

In Formula (BN-1), $Ar^1$ represents an arylene group that may have a substituent Z. $Ar^2$ represents a condensed hydrocarbyl group that may have a substituent Z. Each of $R^{101}$ to $R^{113}$ independently represents a hydrogen atom, an alkyl group, a cycloalkyl group, or a phenyl group that may have a substituent Z.

The substituent Z represents an alkyl group, an alkenyl group, an aryl group, an aromatic heterocyclic group, an alkoxy group, an aryloxy group, a fluorine atom, a silyl group, an amino group, a cyano group or a combination thereof, and a plurality of substituents Z may be bonded to each other to form an aryl ring.)

[2] The light emitting organic thin film of [1], characterized in that, in Formula (PQ-1), two of $R^a$, $R^b$ and $R^c$ represent a methyl group and the remaining one represents a hydrogen atom.

[3] The light emitting organic thin film of [1], characterized in that, in Formula (PQ-1), $R^a$ and $R^c$ represent an alkyl group and $R^b$ represents a hydrogen group.

[4] The light emitting organic thin film of [2] or [3], characterized in that, in Formula (PQ-1), $R^1$ to $R^5$ represent a hydrogen atom.

[5] The light emitting organic thin film of any one of [1] to [4], characterized in that, in Formula (BN-1), $R^{101}$ to $R^{113}$ represent a hydrogen atom.

[6] The light emitting organic thin film of any one of [1] to [5], characterized in that, in Formula (BN-1), $Ar^1$ represents a phenylene group.

[7] The light emitting organic thin film of any one of [1] to [6], characterized in that, in Formula (BN-1), $Ar^2$ represents a naphthyl group, a phenanthryl group or a triphenylenyl group.

[8] The light emitting organic thin film of any one of [1] to [7], wherein in Formula (PQ-1), $R^a$ and $R^c$ represent an alkyl group and $R^b$ represents a hydrogen group, and in Formula (BN-1), $R^{101}$ to $R^{106}$ represent a hydrogen atom, $Ar^1$ represents a phenylene group, and $Ar^2$ represents a naphthyl group, a phenanthryl group or a triphenylenyl group.

[9] A composition including the compound represented by Formula (PQ-1) and the compound represented by Formula (BN-1) of any one of [1] to [8].

[10] An organic electroluminescence device having a pair of electrodes, and an organic layer including a light emitting layer disposed between the electrodes, on a substrate, characterized in that the light emitting layer is the light emitting organic thin film of [1].

[11] The organic electroluminescence device of [10] having a pair of electrodes, and an organic layer including a light emitting layer disposed between the electrodes on a substrate, characterized in that the light emitting layer is the light emitting organic thin film of [1], and the compound represented by Formula (BN-1) of [1] has no peak current value at 100K to 150K as determined by thermally stimulated current of a thin film formed to a film thickness of 100 nm by vacuum deposition of the compound.

[12] The organic electroluminescence device of [10] or [11], characterized in that at least one layer of the organic layer is formed by a coating process using a solution or dispersion.

[13] A display apparatus using the organic electroluminescence device of any one of [10] to [12].

[14] An illumination apparatus using the organic electroluminescence device of any one of [10] to [12].

The organic electroluminescence device of the present invention has low electric power consumption and high external quantum efficiency, and shows excellent durability. Further, the organic electroluminescence device of the present invention has a small difference in voltage increment even under different driving temperatures, and may exhibit stable performance in use of which the driving durability is required in a high temperature environment, such as an in-vehicle use.

DESCRIPTION OF EMBODIMENTS

Figure 1:
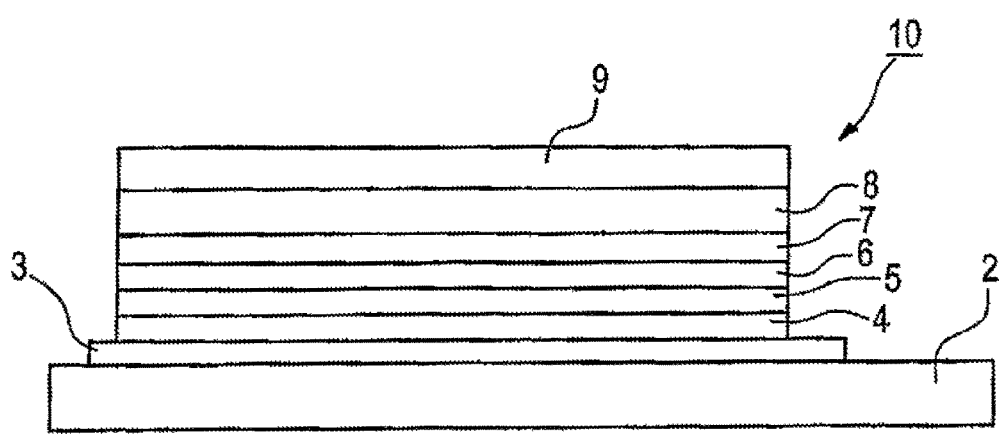
FIG. 1 is a schematic view illustrating an example of the configuration of an organic EL device according to the present invention (the first embodiment).

In the present invention, the substituent Z represents an alkyl group, an alkenyl group, an aryl group, an aromatic heterocyclic group, an alkoxy group, an aryloxy group, a fluorine atom, a silyl group, an amino group, a cyano group or a combination thereof, and a plurality of substituents Z may be bonded to each other to form an aryl ring.

In addition, a hydrogen atom in the following descriptions of Formulae (PQ-1) to (PQ-2), and Formula (BN-1), also includes isotopes (a deuterium atom and the like), and furthermore, an atom constituting a substituent also includes isotopes thereof.

In the present invention, "the number of carbon atoms" of a substituent, such as the alkyl group, is used as a meaning to include the case where the substituent such as the alkyl group may be substituted with an additional substituent, and to include the number of carbon atoms of the additional substituent as well.

The composition and the light emitting organic thin film of the present invention include at least one compound represented by Formula (PQ-1) and at least one compound represented by Formula (BN-1).

The organic electroluminescence device of the present invention includes a pair of electrodes and a light emitting layer between the electrodes, on a substrate, wherein the light emitting layer is the light emitting organic thin film.

It is possible to obtain an organic electroluminescence device having low electric power consumption and high external quantum efficiency and showing excellent durability by using a compound represented by Formula (PQ-1) and a compound represented by Formula (BN-1) in the light emitting layer. It is also possible to obtain an organic electroluminescence device having a small difference in voltage increment even under different driving temperatures.

[Compound Represented by Formula (PQ-1)]

The compound represented by Formula (PQ-1) will be described. Since the red phosphorescent compound has high quantum efficiency, a device with high luminous efficiency may be realized desirably when used in combination with a compound represented by Formula (BN-1). Although the mechanism is not clear, it is possible to obtain a device that has a small difference in driving voltage increment even when used at a different temperature and is preferable in practice.

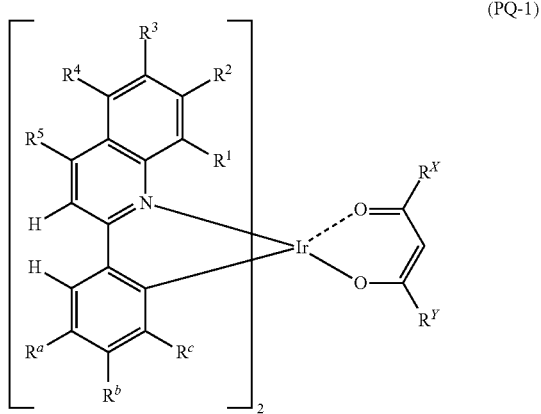

(PQ-1)

(In Formula (PQ-1), each of $R^a$, $R^b$ and $R^c$ independently represents a hydrogen atom or an alkyl group, wherein any one of $R^a$, $R^b$ and $R^c$ represents a hydrogen atom and the remaining two represent an alkyl group. Each of $R^1$ to $R^5$ independently represents a hydrogen atom, an alkyl group, an aryl group, a fluorine atom or a cyano group. Each of $R^x$ and $R^y$ independently represents an alkyl group or a phenyl group.)

Each alkyl group represented by $R^a$, $R^b$ and $R^c$, and $R^1$ to $R^5$ may independently have a substituent, and may be saturated or unsaturated. When the alkyl group has a substituent, the substituent may include the substituent Z, preferably an alkyl group, a phenyl group or a fluorine atom, and more preferably an alkyl group. The alkyl group represented by $R^a$, $R^b$ and $R^c$ is an alkyl group having preferably 1 to 8 carbon atoms, more preferably 1 to 5 carbon atoms, such as a methyl group, an ethyl group, an n-propyl group, an isopropyl group, an isobutyl group, a t-butyl group, an n-butyl group, a cyclohexyl group or the like, preferably a methyl group, an ethyl group, an isobutyl group or a t-butyl group, more preferably a methyl group or an ethyl group, and even more preferably a methyl group.

Each aryl group represented by $R^1$ to $R^5$ may independently be a condensed ring, and may have a substituent. The aryl group represented by $R^1$ to $R^5$ represents an aryl group having preferably 6 to 12 carbon atoms, more preferably 6 to 10 carbon atoms, such as a phenyl group or a naphthyl group, preferably a phenyl group.

In Formula (PQ-1), any one of $R^a$, $R^b$ and $R^c$ represents a hydrogen atom and the remaining two represent an alkyl group. Preferably, $R^b$ or $R^c$ represents a hydrogen atom, and more preferably $R^b$ represents a hydrogen atom.

In Formula (PQ-1), it is preferred that two of $R^a$, $R^b$ and $R^c$ represent a methyl group, and the remaining one represents a hydrogen atom.

More preferably, $R^a$ and $R^c$ represent an alkyl group and $R^b$ represents a hydrogen group, and even more preferably, $R^a$ and $R^c$ represent a methyl group and $R^b$ represents a hydrogen atom.

It is preferred that $R^1$ to $R^5$ represent a hydrogen atom.

Each alkyl group represented by $R^x$ and $R^y$ may independently have a substituent, and may be saturated or unsaturated. When the alkyl group has a substituent, the substituent may include the substituent Z, preferably a phenyl group, an aromatic heterocyclic group, a fluorine atom, a silyl group, an amino group, a cyano group or a combination thereof, and more preferably a phenyl group, a fluorine atom or a cyano group. The alkyl group represented by $R^x$ and $R^y$ is an alkyl group having preferably 1 to 8 carbon atoms, more preferably 1 to 5 carbon atoms, such as a methyl group, an ethyl group, an n-propyl group, an isopropyl group, an isobutyl group, a t-butyl group, an n-butyl group, a cyclohexyl group, or the like, preferably a methyl group, an ethyl group, an isobutyl group or a t-butyl group, more preferably a methyl group.

The alkyl group represented by the substituent Z is an alkyl group preferably having 1 to 8 carbon atoms, more preferably 1 to 5 carbon atoms, such as a methyl group, an ethyl group, an n-propyl group, an isopropyl group, an isobutyl group, a t-butyl group, an n-butyl group, a cyclopropyl group, or the like, preferably a methyl group, an ethyl group, an isobutyl group or a t-butyl group, and more preferably a methyl group.

The alkenyl group represented by the substituent Z is an alkenyl group preferably having 2 to 8 carbon atoms, more preferably 2 to 5 carbon atoms, such as a vinyl group, an n-propenyl group, an isopropenyl group, an isobutenyl group, an n-butenyl group, or the like, and preferably a vinyl group or an n-propenyl group.

The aryl group represented by the substituent Z is an aryl group preferably having 6 to 30 carbon atoms, such as a phenyl group, a naphthyl group, an anthracenyl group, a tetracenyl group, a pyrenyl group, a perylenyl group, a triphenylenyl group or a chrysenyl group, and more preferably a phenyl group, a naphthyl group, an anthracenyl group or a chrysenyl group.

The aromatic heterocyclic group represented by the substituent Z is an aromatic heterocyclic group preferably having 4 to 30 carbon atoms, such as pyridine, pyrazine, pyrimidine, pyridazine, triazine, thiophene, furan, oxazole, thiazole, imidazole, pyrazole, triazole, oxadiazole, thiadiazole, or the like.

The alkoxy group represented by the substituent Z is an alkoxy group preferably having 1 to 8 carbon atoms, more preferably 1 to 5 carbon atoms, such as a methoxy group, an ethoxy group, an n-propyloxy group, an isopropyloxy group, or the like, preferably a methoxy group or an ethoxy group, and more preferably a methoxy group.

The aryloxy group represented by the substituent Z is an aryloxy group preferably having 6 to 30 carbon atoms, such as a phenoxy group or a naphthoxy group, preferably a phenoxy group.

The aryl group formed by a plurality of substituents Z bound with each other may include a phenyl ring or a pyridine ring, preferably a phenyl ring.

Preferably, the compound represented by Formula (PQ-1) is a compound represented by the following Formula (PQ-2).

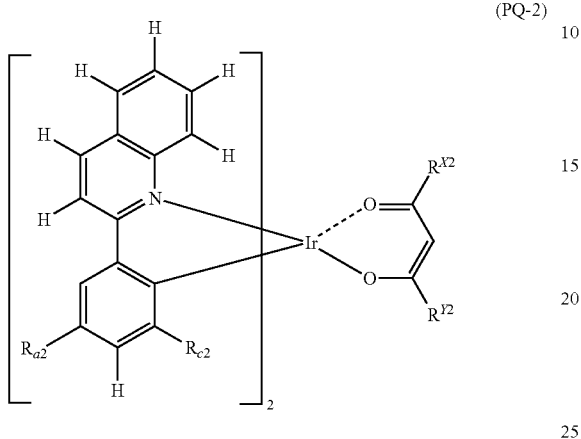

(PQ-2)

(In Formula (PQ-2), each of $R_{a2}$ and $R_{c2}$ independently represents an alkyl group. Each of $R^{X2}$ and $R^{Y2}$ independently represents an alkyl group).

The alkyl group represented by $R_{a2}$ and $R_{c2}$ has the same meaning as defined for the above $R_a$ and $R_c$, and preferred ranges thereof are also the same.

The alkyl group represented by $R^{X2}$ and $R^{Y2}$ has the same meaning as defined for the above $R^X$ and $R^Y$ in Formula (PQ-1), and preferred ranges thereof are also the same.

Particular examples of the compound represented by Formula (PQ-1) are listed hereinafter, but are not limited thereto.

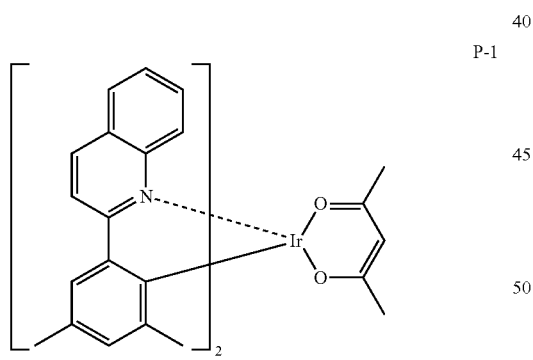

P-1

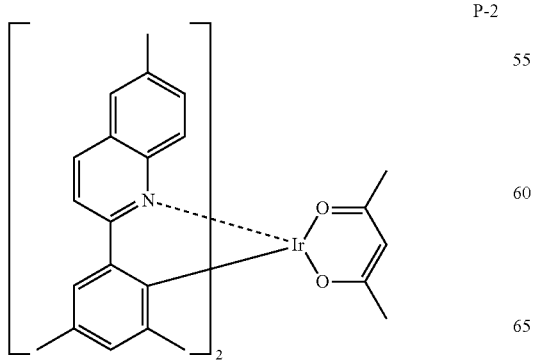

P-2

-continued

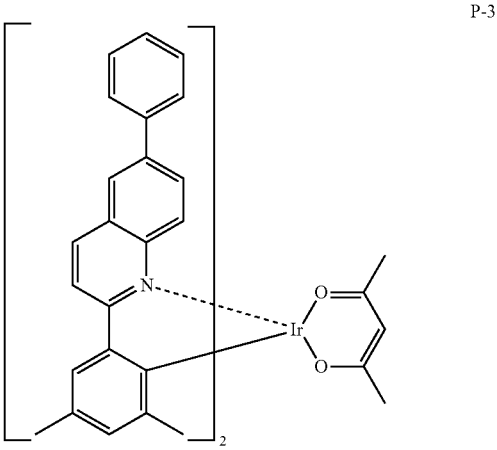

P-3

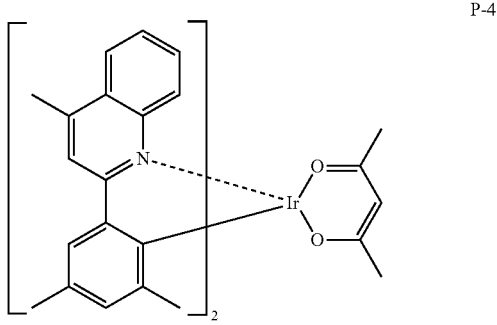

P-4

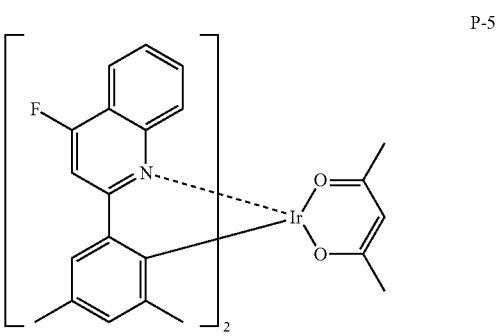

P-5

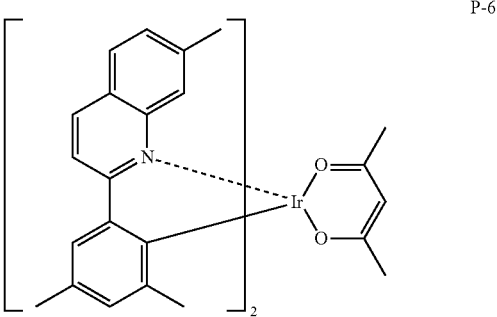

P-6

P-7
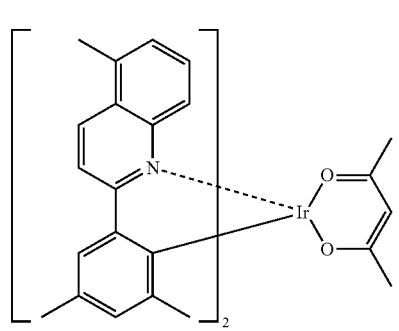
P-8
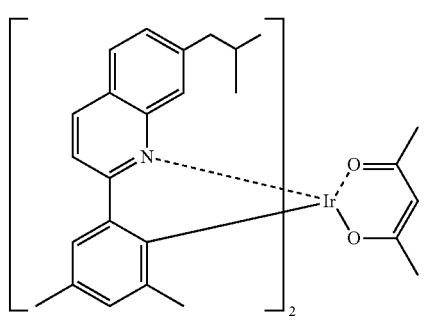
P-9
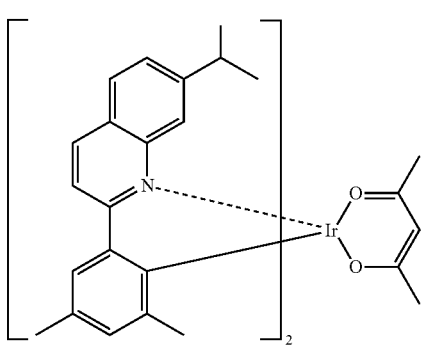
P-10
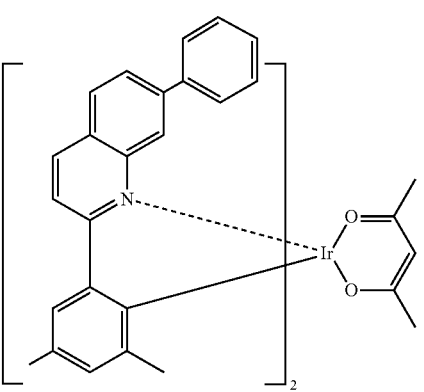
P-11
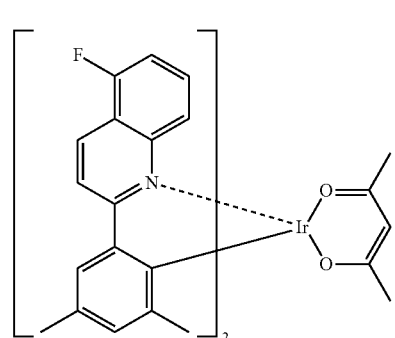
P-12
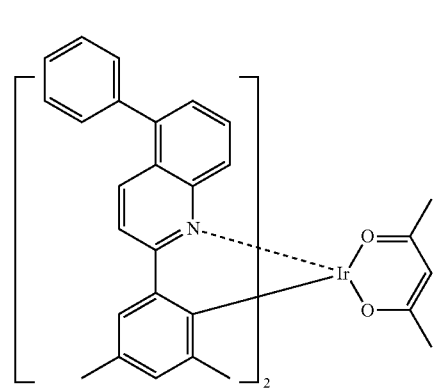
P-13
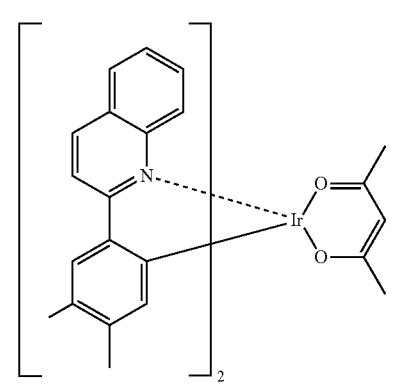
P-14
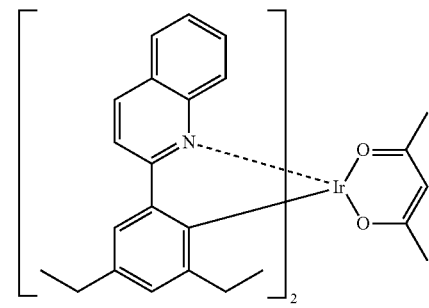

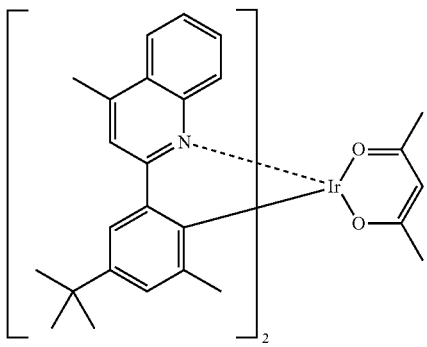

P-15

[Compound Represented by Formula (BN-1)]

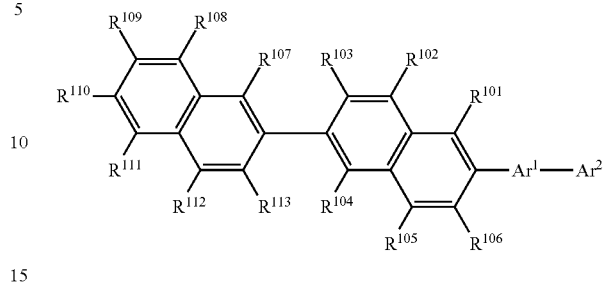

(BN-1)

Compounds exemplified as the compounds represented by the above Formula (PQ-1) may be synthesized by various methods, for example, a method described in Japanese Patent No. 3929632, and the like. For example, the compounds may be synthesized using 2-phenylquinoline as a starting raw material by a method described on page 18, lines 2 to 13 of Japanese Patent No. 3929632, or using 2-(2-naphthyl)quinoline as a starting raw material by a method described on page 18, line 14 to page 19, line 8 of Japanese Patent No. 3929632.

In the present invention, it is preferable that the compound represented by Formula (PQ-1) is contained in the light emitting organic thin film in an amount of preferably 0.1 to 30 mass %, preferably 2 to 20 mass %, and particularly preferably 5 to 15 mass % in the light emitting organic thin film.

In addition, it is preferably that each of Cl, Br and I is contained in the light emitting organic thin film in an amount of 100 ppm or less, more preferably 0 ppm to 40 ppm, and particularly preferably 0 ppm to 10 ppm. When each of Cl, Br and I is contained in the light emitting organic thin film in an amount of 100 ppm or less, it is possible to inhibit deterioration during light emission and to improve the durability of a device. It is possible to obtain an amount of Cl, Br, I of 100 ppm or less by repeating purification of materials.

In the present invention, the compound represented by Formula (PQ-1) is contained in the light emitting organic thin film, but the use thereof is not limited thereto and the compound may be contained in any one layer of the organic layer.

The compound represented by Formula (BN-1) will be described.

Since the compound of Formula (BN-1) has a condensed hydrocarbyl group and is a material having high rigidity and durability, a light emitting layer or a luminescence device with high durability and quantum efficiency may be realized preferably when used in combination with a compound represented by Formula (PQ-1) for a light emitting organic thin film. Although the mechanism is not clear, it is possible to fabricate a device that has a small difference in driving voltage increment even when used at a different temperature of usage environment and is preferable in practice.

(In Formula (BN-1), $Ar^1$ represents an arylene group that may have a substituent Z. $Ar^2$ represents a condensed hydrocarbyl group that may have a substituent Z. Each of $R^{101}$ to $R^{113}$ independently represents a hydrogen atom, alkyl group, cycloalkyl group, or a phenyl group that may have a substituent Z.

The substituent Z represents an alkyl group, an alkenyl group, an aryl group, an aromatic heterocyclic group, an alkoxy group, an aryloxy group, a fluorine atom, a silyl group, an amino group, a cyano group or a combination thereof, and a plurality of substituents Z may be bonded to each other to form an aryl ring.)

The arylene group that may have a substituent Z, represented by $Ar^1$, is a phenylene group, a biphenylene group, a terphenylene group, a naphthalene group, a phenanthrenediyl group, a triphenylenediyl group, and preferably a p-phenylene group or a m-phenylene group that may have a substituent Z, and more preferably a m-phenylene group that may have a substituent Z.

The substituent Z of $Ar^1$ preferably represents an alkyl group, an aryl group, a fluoro group, a cyano group, more preferably an alkyl group or an aryl group, and even more preferably a phenyl group, a phenanthryl group, a t-butyl group. From the viewpoint of the durability of a device, it is particularly preferred that $Ar^1$ is a m-phenylene group having a substituent Z at 5-position.

The condensed hydrocarbyl group that may have a substituent Z, represented by $Ar^2$, is a condensed hydrocarbyl group preferably having 10 to 18 carbon atoms, preferably a naphthyl group, a phenanthryl group, a triphenylenyl group, an anthracenyl group, a tetracenyl group, a chrysenyl group, more preferably a naphthyl group, a phenanthryl group, a triphenylenyl group, even more preferably a naphthyl group or a phenanthryl group, and most preferably a naphthyl group.

The substituent Z in the case of $Ar^2$ having a substituent Z is preferably an aryl group, an alkyl group, a fluoro group, a cyano group, more preferably an aryl group, and even more preferably a phenyl group.

The alkyl group represented by $R^{101}$ to $R^{113}$ is an alkyl group preferably having 1 to 10 carbon atoms, more preferably 1 to 5 carbon atoms, such as a methyl group, an ethyl group, an n-propyl group, an isopropyl group, an isobutyl group, a t-butyl group, an n-butyl group, preferably a methyl group, an ethyl group, an isobutyl group or a t-butyl group, and more preferably a methyl group.

The cycloalkyl group represented by $R^{101}$ to $R^{113}$ is a cycloalkyl group preferably having 3 to 10 carbon atoms, such as a cyclopropyl group, a cyclobutyl group, a cyclopentyl group, a cyclohexyl group, or the like, preferably a cyclohexyl group.

In the phenyl group that may have a substituent Z, represented by $R^{101}$ to $R^{113}$, the substituent Z may be exemplified by the above-described substituent Z. Preferably, the phenyl group that may have a substituent Z, represented by $R^{101}$ to $R^{110}$, is a phenyl group having a cyano group or a trifluoromethyl group, or a non-substituted phenyl group.

In Formula (BN-1), from the viewpoint of the durability of a device, $R^{101}$ to $R^{106}$ preferably represent a hydrogen atom. More preferably, $R^{101}$ to $R^{106}$, $R^{107}$, $R^{108}$, $R^{112}$ and $R^{113}$ preferably represent a hydrogen atom. When $R^{101}$ to $R^{106}$ have a substituent Z, from the viewpoint of the durability of a device, $R^{109}$, $R^{110}$ or $R^{111}$ preferably have a substituent Z, and more preferably $R^{110}$ has a substituent Z.

In Formula (BN-1), it is preferred that the substituent Z represented by $R^{101}$ to $R^{113}$ is a methyl group, a t-butyl group, a cyclohexyl group, a phenyl group, more preferably a t-butyl group, a phenyl group, and even more preferably a phenyl group, and those substituents may further contain a substituent Z (preferably, a cyano group, a trifluoromethyl group.)

In Formula (BN-1), preferably, $Ar^1$ represents a phenylene group that may have a substituent Z, $Ar^2$ represents a C10 to C18 condensed hydrocarbyl group that may have a substituent Z, $R^{101}$ to $R^{106}$ represent a hydrogen atom, each of $R^{107}$ to $R^{113}$ independently represents a hydrogen atom, an alkyl group, a cycloalkyl group, or a phenyl group that may have a substituent Z, more preferably, $Ar^1$ represents a phenylene group that may have an alkyl group, $Ar^2$ represents a naphthyl group, a phenanthryl group or a triphenylenyl group that may have a substituent Z, $R^{101}$ to $R^{106}$ represent a hydrogen atom, each of $R^{107}$ to $R^{113}$ independently represents a hydrogen atom, an alkyl group, a cycloalkyl group, or a phenyl group that may have a substituent Z, even more preferably, $Ar^1$ represents a phenylene group that may have an alkyl group, $Ar^2$ represents a naphthyl group, a phenanthryl group or a triphenylenyl group that may have a substituent Z, $R^{101}$ to $R^{106}$ represent a hydrogen atom, each of $R^{107}$ to $R^{113}$ independently represents a hydrogen atom, an alkyl group, a cycloalkyl group, or a phenyl group that may have a substituent Z, and particularly preferably, $Ar^1$ represents a phenylene group that may have an alkyl group, $Ar^2$ represents an unsubstituted naphthyl group, an unsubstituted phenanthryl group or an unsubstituted triphenylenyl group, $R^{101}$ to $R^{106}$, $R^{107}$, $R^{108}$, $R^{112}$ and $R^{113}$ represent a hydrogen atom, and each of $R^{109}$, $R^{110}$ and $R^{111}$ independently represents a hydrogen atom, an alkyl group, a cycloalkyl group, or a phenyl group that may have a substituent Z.

The compound represented by Formula (BN-1) preferably has a molecular weight of 400 to 1000, more preferably 450 to 800, and even more preferably 500 to 700.

The compound represented by Formula (BN-1) preferably has a glass transition temperature (Tg) of 80° C. to 400° C., more preferably 100° C. to 400° C., and even more preferably 120° C. to 400° C.

When Formula (BN-1) has hydrogen atoms, such hydrogen atoms also include isotopes (a deuterium atom and the like). In this case, all hydrogen atoms in the compound may be substituted by isotopes, or the compound may be a mixture partially containing isotopes.

Hereinafter, particular examples of the compound represented by Formula (BN-1) will be exemplified but the present invention is not limited thereto.

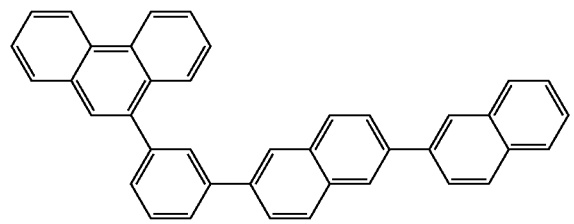

B-1

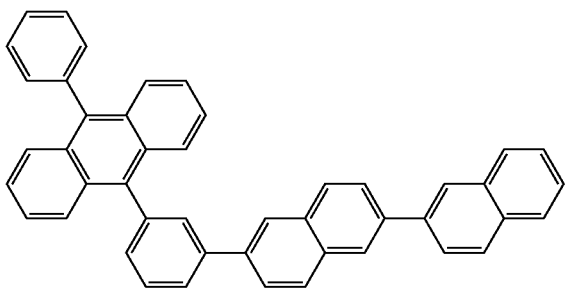

B-2

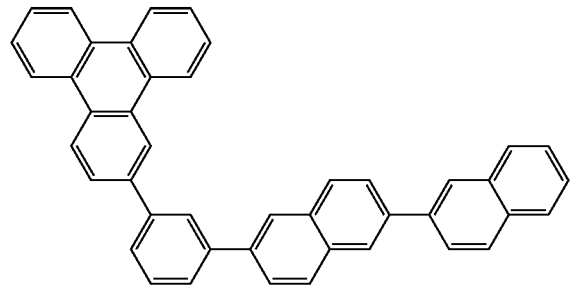

B-3

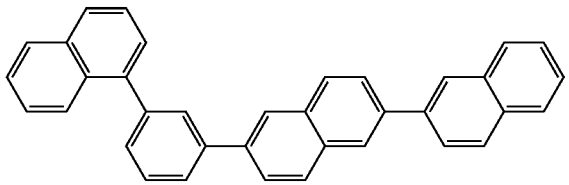

B-4

-continued
B-5
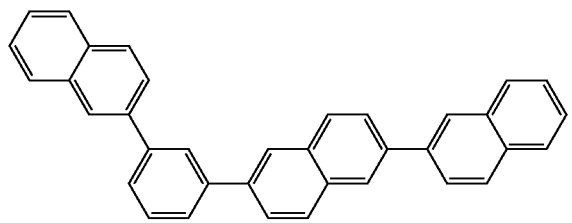
B-6
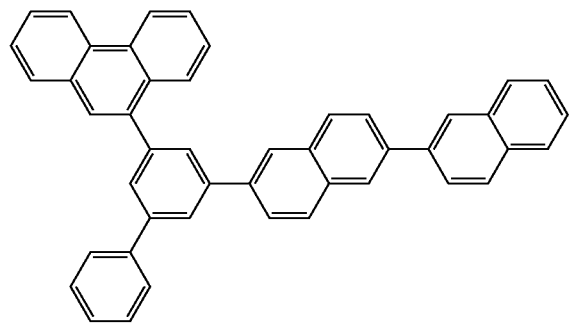
B-7
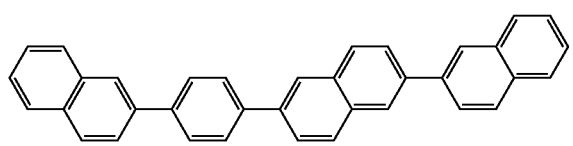
B-8
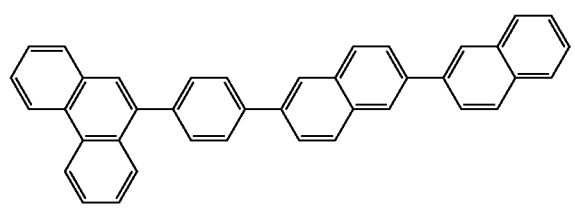
B-9
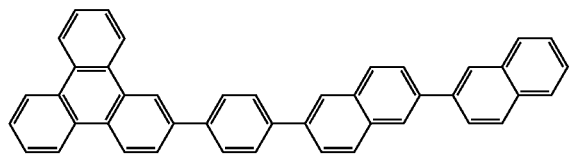
B-10
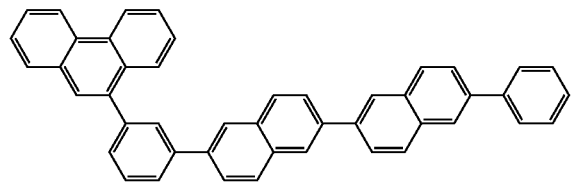
B-11
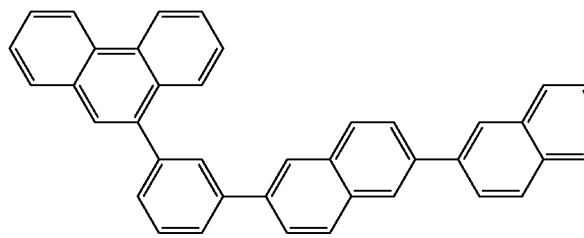
B-12
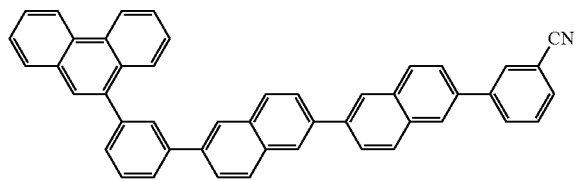
B-13
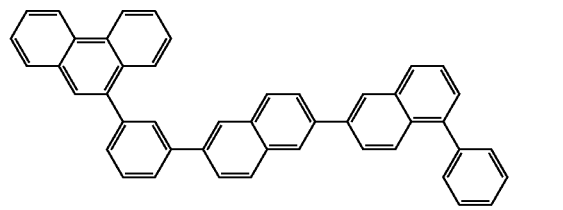
B-14
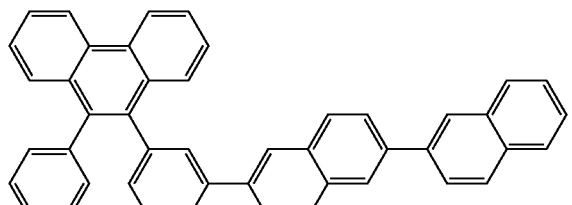
B-15
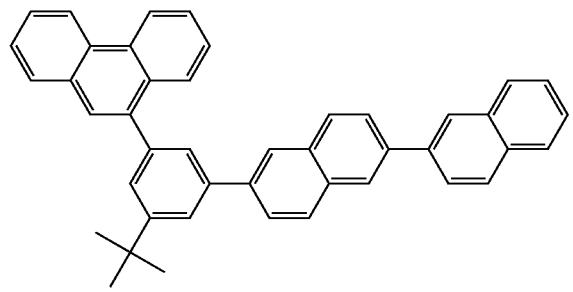

-continued

B-16

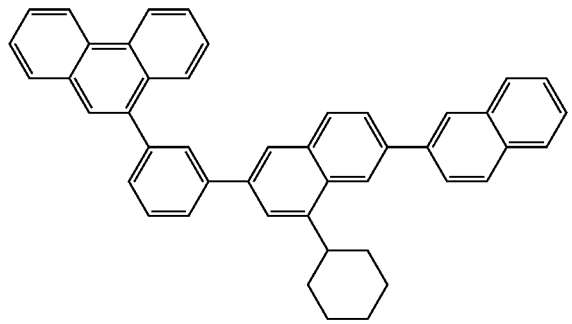

B-17

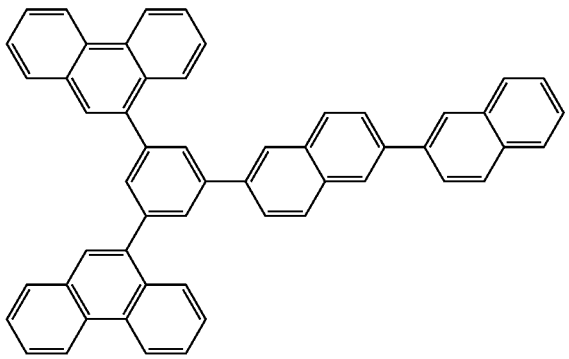

B-18

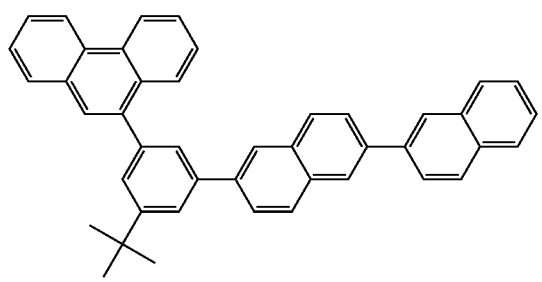

B-19

B-20

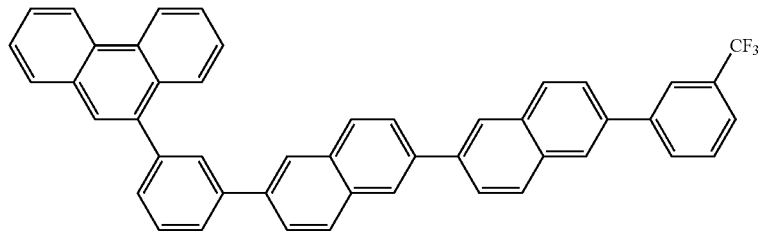

The above-exemplified compounds represented by the above Formula (BN-1) may be synthesized by applying a method described in US 2009/0009065. For example, Compound B-1 may be synthesized by a method described in [0307] of US Patent Application No. 2009/0009065 using 2-bromo-6-(2-naphthyl)naphthalene and 3-(9-phenanthryl)phenyl borate as starting materials.

In the present invention, the compound represented by Formula (BN-1) is contained in a light emitting organic thin film. In the luminescence device of the present invention, use of the compound is not limited and the compound may be further contained in any one layer within the organic layer. Preferably, the compound represented by Formula (BN-1) may be introduced to one or more layers among a light emitting layer, a hole injection layer, a hole transporting layer, an electron transporting layer, an electron injection layer, an exciton blocking layer and a charge blocking layer.

In the light emitting organic thin film of the present invention, it is preferable that $R^a$ and $R^b$ represent alkyl groups and $R^b$ represents a hydrogen atom in Formula (PQ-1), and $R^{101}$ to $R^{106}$ represent a hydrogen atom, $Ar^1$ represents a phenylene group, and $Ar^2$ represents a naphthyl group, phenanthryl group or triphenylenyl group, in Formula (BN-1).

The content of the compound represented by Formula (BN-1) in the light emitting organic thin film of the present invention is preferably 0.1 to 99 mass %, more preferably 1 to 95 mass %, and even more preferably 10 to 95 mass %, based on the total mass of the light emitting organic thin film.

In addition, in the luminescence device of the present invention, in the case of the compound represented by Formula (BN-1) contained in any one layer other than the light emitting layer formed of the light emitting organic thin film, the content is preferably 10 to 100 mass %, more preferably 30 to 100 mass %, and even more preferably 50 to 100 mass %.

[Light Emitting Layer Containing a Compound Represented by Formula (PQ-1) and a Compound Represented by Formula (BN-1)]

The present invention also relates to a light emitting layer containing a compound represented by Formula (PQ-1) and a compound represented by Formula (BN-1). The light emitting layer of the present invention may be applied to an organic electroluminescence device.

[Composition Containing a Compound Represented by Formula (PQ-1) and a Compound Represented by Formula (BN-1)]

The present invention also relates to a composition containing a compound represented by Formula (PQ-1) and a compound represented by Formula (BN-1).

In the composition of the present invention, the content of the compound represented by Formula (PQ-1) is preferably 1 to 40 mass %, and more preferably 5 to 20 mass %.

In the composition of the present invention, the content of the compound represented by Formula (BN-1) is preferably 50 to 95 mass %, and more preferably 70 to 90 mass %.

Other ingredients that may be further contained in the composition of the present invention may be organic materials or inorganic materials, and the materials exemplified as host materials, fluorescence emitting materials, phosphorescence emitting materials and hydrocarbon materials hereinafter may be used as the organic materials.

The composition of the present invention may form an organic layer of an organic electroluminescence device by a dry film forming method such as deposition or sputtering, or by a wet film forming method such as ink-jet, spin coating, bar coating, transferring or printing.

Further, the present invention relates to a method for selection of a compound represented by Formula (BN-1) for use in a light emitting layer of an organic electroluminescence device having a pair of electrodes, and an organic layer including a light emitting layer disposed between the electrodes on a substrate, wherein the light emitting layer contains a compound represented by Formula (PQ-1) and a compound represented by Formula (BN-1), characterized by selecting a compound having no peak current value at 100 K to 150 K as determined by thermally stimulated current of a thin film formed to a film thickness of 100 nm by vacuum deposition of the compound. By the selection, it is possible to provide a device with higher durability.

[Organic Electroluminescence Device]

The device of the present invention will be described in detail.

The organic electroluminescence device of the present invention has, on a substrate, a pair of electrodes and a light emitting layer between the electrodes, wherein the light emitting layer is the light emitting organic thin film of the present invention. The light emitting organic thin film of the present invention contains a compound represented by Formula (BN-1) and a compound represented by Formula (PQ-1).

In the organic electroluminescence device of the present invention, the light emitting layer is an organic layer and the device may have a plurality of organic layers.

Due to properties of the luminescence device, at least one electrode of the anode and the cathode is preferably transparent or semi-transparent.

FIG. 1 shows an example of the configuration of an organic electroluminescence device according to the present invention. The organic electroluminescence device 10 of the present invention as shown in FIG. 1, has a light emitting layer 6 between an anode 3 and a cathode 9 on a supporting substrate 2. Particularly, a hole injection layer 4, a hole transporting layer 5, a light emitting layer 6, a hole blocking layer 7, and an electron transporting layer 8 are laminated in this order between the anode 3 and the cathode 9.

<Configuration of Organic Layer>

There is no particular limitation in the configuration of the organic layer, and the organic layer may be selected adequately depending on the use and purpose of an organic electroluminescence device, but it is preferred to be formed on the transparent electrode or on the back electrode. In this case, the organic layer is formed on the front surface or one surface of the transparent electrode or the back electrode.

The shape, size and thickness of the organic layer are not particularly limited and may be selected adequately depending on the purpose.

Particular examples of the configuration will be described hereinafter but the present invention is not limited thereto.

Anode/hole transporting layer/light emitting layer/electron transporting layer/cathode, Anode/hole transporting layer/light emitting layer/second electron transporting layer (hole blocking layer)/first electron transporting layer/cathode, Anode/hole transporting layer/light emitting layer/second electron transporting layer (hole blocking layer)/first electron transporting layer/electron injection layer/cathode, Anode/hole injection layer/hole transporting layer (electron blocking layer)/light emitting layer/second electron transporting layer (hole blocking layer)/first electron transporting layer/cathode, Anode/hole injection layer/first hole transporting layer/second hole transporting layer (electron blocking layer)/light emitting layer/second electron transporting layer (hole blocking layer)/first electron transporting layer/cathode.

The device configuration, substrate, cathode, and anode of the organic electroluminescence device are described in detail in, for example, Japanese Patent Application Laid-Open No. 2008-270736, and the subject matters described in the publication may be applied to the present invention.

<Substrate>

It is preferred that the substrate used in the present invention is a substrate which does not scatter or decay light generated from the organic layer. In the case of organic materials, those excellent in heat resistance, dimensional stability, solvent resistance, electrical insulating property and processability are preferred.

<Anode>

Typically, the anode may have a function as an electrode for supplying a hole into the organic layer. The anode is not particularly limited with respect to a shape, a structure, a size and the like, and may be appropriately selected among known electrode materials depending upon a use or purpose of the luminescence device. As described above, the anode is usually provided as a transparent anode.

<Cathode>

Typically, the cathode may have a function as an electrode for injecting an electron into the organic layer. The cathode is not particularly limited with respect to a shape, a structure, a size and the like, and may be appropriately selected among known electrode materials depending upon a use or purpose of the luminescence device.

With respect to the substrate, the anode and the cathode, the subject matters described in paragraph Nos. [0070] to [0089] of Japanese Patent Application Laid-Open No. 2008-270736 may be applied to the present invention.

<Organic Layer>

The organic layer of the present invention will be described in detail.

—Formation of Organic Layer—

In the organic electroluminescence device of the present invention, each organic layer may be formed suitably by any one of dry film forming methods, such as deposition or sputtering, and coating processes, such as transfer coating, printing, inkjet coating, spin coating, bar coating, and the like.

(Light Emitting Layer)

<Light Emitting Material>

It is preferred that the light emitting material in the invention is a compound represented by Formula (PQ-1).

The light emitting material in the light emitting layer is generally contained in an amount of 0.1 mass % to 50 mass % based on the total mass of the compounds forming the light emitting layer. However, from the viewpoints of durability and external quantum efficiency, the material is contained in an amount of preferably 1 mass % to 50 mass %, more preferably 2 mass % to 40 mass %.

A thickness of the light emitting layer is not particularly limited, but typically, is preferably 2 nm to 500 nm, and among them, from the viewpoint of external quantum efficiency, the thickness of the light emitting layer is more preferably 3 nm to 200 nm, and even more preferably 5 nm to 100 nm.

The light emitting material in the device of the present invention may further include any light emitting layer other than the light emitting layer of the present invention, and such a light emitting layer may be composed of a light emitting material alone or a combination of a host material with a light emitting material. The light emitting material may be a fluorescence emitting material or a phosphorescence emitting material, and one kind of dopant or two or more kinds of dopants may be used. Preferably, the host material is a charge transporting material. One kind of host material or two or more kinds of host materials may be used, and for example, a combination of an electron transporting host material with a hole transporting host material may be used. In addition, a material having no charge transportability and light emitting property may be contained in the light emitting layer. In the light emitting layer of the device of the present invention, a combination using a compound represented by Formula (BN-1) and a compound represented by Formula (PQ-1) are essentially contained as the host material.

In addition, the light emitting layer may be a single layer or multilayer having two layers or more. In the case of a multilayered light emitting layer, a compound represented by Formula (BN-1) and a compound represented by Formula (PQ-1) may be contained in two or more light emitting layers. Further, each light emitting layer may emit a different color.

<Host Material>

As the host material used in the present invention, the compound represented by Formula (BN-1) is preferred.

The compound represented by Formula (BN-1) can transport positive and negative charges, such as holes and electrons, and makes a carrier balance between holes and electrons better through the combination with a compound represented by Formula (PQ-1). Therefore, although the compound has a carbazole group, it is possible to improve driving durability. Further, even at a different driving temperature, it is possible to reduce a difference in voltage increment.

As the host material used in the present invention, the compounds listed hereinafter may be further contained. For example, examples thereof may include, for example, conductive polymer oligomers such as pyrrole, indole, carbazole, CBP (4,4'-di(9-carbazoyl)biphenyl), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilben, silazane, aromatic tertiary amine compounds, styrylamine compounds, polypyrine-based compounds, polysilane-based compounds, poly(N-vinylcarbazole), aniline-based copolymers, thiophene oligomers, and polythiophene, organosilane, carbon film, pyridine, pyrimidine, triazine, imidazole, pyrazole, triazole, oxazole, oxadiazole, fluorenone, anthraquinodimethane, anthrone, diphenylquinone, thiopyrane dioxide, carbodiimide, fluorenylidene methane, distyrylpyrazine, fluoro-substituted aromatic compounds, heterocyclic tetracarboxylic acid anhydrides such as naphthalene, perylene, or the like, phthalocyanine, metal complexes of 8-quinolinol derivatives or metal phthalocyanine, various metal complexes represented by metal complexes having benzoxazole or benzothiazole as a ligand, and derivatives (which may have a substituent or condensed ring) thereof.

In the light emitting layer of the present invention, it is preferable that a lowest triplet excited state ($T_1$) energy of the host material (also containing the compound represented by Formula (BN-1)) is higher than $T_1$ energy of the phosphorescence emitting material, from the viewpoints of color purity, luminous efficiency and driving durability.

In addition, a content of the host compound in the present invention is not particularly limited, but is preferably 15 mass % to 95 mass % based on the total mass of the compounds forming the light emitting layer, from the viewpoints of luminous efficiency and driving voltage.

When the compound represented by Formula (BN-1) is introduced to a layer (e.g. a charge transporting layer) other than a light emitting layer, the compound is contained in the layer preferably in an amount of 10 mass % to 100 mass %, and more preferably 30 mass % to 100 mass %.

(Fluorescence Emitting Material)

Examples of the fluorescence emitting material that may be used in the present invention include benzoxazole derivatives, benzoimidazole derivatives, benzothiazole derivatives, styrylbenzene derivatives, polyphenyl derivatives, diphenylbutadiene derivatives, tetraphenylbutaidene derivatives, naphthalimide derivatives, cumarine derivatives, condensed aromatic compounds, perinone derivatives, oxadizaole derivatives, oxazine derivatives, aldazine derivatives, pyralyzine derivatives, cyclopentadiene derivatives, bisstyrylanthracene derivatives, quinacridone derivatives, pyrrolopyridine derivatives, thiadiazopyridine derivatives, cyclopentadiene derivatives, styrylamine derivatives, diketopyrrolopyrrole derivatives, aromatic dimethylidene compounds, various complexes represented by complexes of 8-quinolinol derivatives or complexes of pyromethene derivatives, polymer compounds such as polythiophene, polyphenylene, polyphenylene vinylene, or the like, compounds such as organosilane derivatives, or the like.

(Phosphorescence Emitting Material)

The phosphorescence emitting materials that may be used in the present invention include, besides a compound represented by Formula (PQ-1), for example, phosphorescence emitting compounds described in patent documents, such as U.S. Pat. No. 6,303,238B1, U.S. Pat. No. 6,097,147, WO00/57676, WO00/70655, WO01/08230, WO01/39234A2, WO01/41512A1, WO02/02714A2, WO02/15645A1, WO02/44189A1, WO05/19373A2, Japanese Patent Application Laid-Open No. 2001-247859, Japanese Patent Application Laid-Open No. 2002-302671, Japanese Patent Application Laid-Open No. 2002-117978, Japanese Patent Application Laid-Open No. 2003-133074, Japanese Patent Application Laid-Open No. 2002-235076, Japanese Patent Application Laid-Open No. 2003-123982, Japanese Patent Application Laid-Open No. 2002-170684, EP1211257, Japanese Patent Application Laid-Open No. 2002-226495, Japanese Patent Application Laid-Open No. 2002-234894, Japanese Patent Application Laid-Open No. 2001-247859, Japanese Patent Application Laid-Open No. 2001-298470, Japanese Patent Application Laid-Open No. 2002-173674, Japanese Patent Application Laid-Open No. 2002-203678, Japanese Patent Application Laid-Open No. 2002-203679, Japanese Patent Application Laid-Open No. 2004-357791, Japanese Patent Application Laid-Open No. 2006-256999, Japanese Patent Application Laid-Open No. 2007-19462, Japanese Patent Application Laid-Open No. 2007-84635, Japanese Patent Application Laid-Open No. 2007-96259, or the like, and more preferred light emitting dopants among them include Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes. Particularly preferably, the phosphorescence emitting material is an Ir complex, Pt complex or Re complex, and among them, an Ir complex, Pt complex or Re complex containing at least one coordination type of metal-carbon bonding, metal-nitrogen bonding, metal-oxygen bonding and metal-sulfur bonding is preferred. In addition, from the viewpoints of luminous efficiency, driving durability, chromaticity, or the like, an Ir complex, Pt complex or Re complex containing a tridentate or multi-dentate ligand is particularly preferred.

A content of the phosphorescence emitting material in the light emitting layer is preferably 0.1 mass % to 50 mass %, more preferably 0.2 mass % to 50 mass %, even more preferably 0.3 mass % to 40 mass %, and most preferably 20 mass % to 30 mass %, based on the total mass of the light emitting layer.

The content of the phosphorescence emitting material (a compound represented by Formula (PQ-1) and/or a phosphorescence emitting material used in combination) that may be used in the present invention is preferably 0.1 mass % to 50 mass %, more preferably 1 mass % to 40 mass %, and most preferably 5 mass % to 30 mass %, based on the total mass of the light emitting layer. Particularly, in the range of 5 mass % to 30 mass %, the chromaticity of light emission of the corresponding organic electroluminescence device is less dependent on the concentration of the added phosphorescence emitting material.

Most preferably, the organic electroluminescence device of the present invention contains at least one of compounds represented by Formula (PQ-1) in an amount of 5 to 30 mass % based on the total mass of the light emitting material.

A thickness of the light emitting layer is not particularly limited, but typically, is preferably 1 nm to 500 nm, more preferably 5 nm to 200 nm, and even more preferably 10 nm to 100 nm.

(Charge Transporting Layer)

A charge transporting layer refers to a layer in which charge transport occurs when applying voltage to an organic electroluminescence device. Particularly, the charge transporting layer includes a hole injection layer, a hole transporting layer, an electron blocking layer, a light emitting layer, a hole blocking layer, an electron transporting layer or an electron injection layer. Preferably, the charge transporting layer is a hole injection layer, a hole transporting layer, an electron blocking layer or a light emitting layer. When a charge transporting layer formed by a coating method is a hole injection layer, a hole transporting layer, an electron blocking layer or a light emitting layer, it is possible to fabricate a low-cost, high-efficiency organic electroluminescence device. More preferably, the charge transporting layer is a hole injection layer, a hole transporting layer or an electron blocking layer.

—Hole Injection Layer and Hole Transporting Layer—

A hole injection layer and a hole transporting layer are layers having a function of accepting a hole from an anode or anode side and transporting the hole to a cathode side.

A hole injection material and a hole transporting material used in these layers may be a low-molecular weight compound or a polymer compound.

Particularly, it is preferred that the hole injection layer and the hole transporting layer are layers containing a pyrrole derivative, a carbazole derivative, a pyrrole derivative, a triazole derivative, an oxazole derivative, an oxadiazole derivative, an imidazole derivative, a polyarylalkane derivative, a pyrazoline derivative, a pyrazolone derivative, a phenylene diamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, a phthalocyanine-based compound, a polypyrine-based compound, a thiophene derivative, an organosilane derivative, carbon, various metal complexes such as an Ir complex, or the like.

An electron-accepting dopant may be contained in the hole injection layer or the hole transporting layer in the organic electroluminescence device of the present invention. As the electron accepting dopant introduced to the hole injection layer or the hole transporting layer, any inorganic compound or organic compound may be used as long as the compound is electron accepting and functions to oxidize an organic compound.

Particularly, the inorganic compound includes a metal halide such as ferric chloride or aluminum chloride, gallium chloride, indium chloride, antimony pentachloride, or the like, and a metal oxide such as vanadium pentaoxide, molybdenum trioxide, or the like.

In the case of an organic compound, a compound having a nitro group, a halogen, a cyano group, a trifluoromethyl group, or the like as a substituent, a quinone-based compound, an acid anhydride-based compound, fullerene, or the like may be suitably used.

Besides, compounds described in Japanese Patent Application Laid-Open No. Hei 6-212153, Japanese Patent Application Laid-Open No. Hei 11-111463, Japanese Patent Application Laid-Open No. Hei 11-251067, Japanese Patent Application Laid-Open No. 2000-196140, Japanese Patent Application Laid-Open No. 2000-286054, Japanese Patent Application Laid-Open No. 2000-315580, Japanese Patent Application Laid-Open No. 2001-102175, Japanese Patent Application Laid-Open No. 2001-160493, Japanese Patent Application Laid-Open No. 2002-252085, Japanese Patent Application Laid-Open No. 2002-56985, Japanese Patent Application Laid-Open No. 2003-157981, Japanese Patent Application Laid-Open No. 2003-217862, Japanese Patent Application Laid-Open No. 2003-229278, Japanese Patent Application Laid-Open No. 2004-342614, Japanese Patent Application Laid-Open No. 2005-72012, Japanese Patent Application Laid-Open No. 2005-166637, Japanese Patent Application Laid-Open No. 2005-209643, or the like may be used adequately.

Among the compounds, hexacyanobutadiene, hexacyanobenzene, tetracyanoethylene, tetracyanoquinodimethane, tetrafluorotetracyanoquinodimethane, p-fluoranyl, p-chloranyl, p-bromanyl p-benzoquinone, 2,6-dichlorobenzoquinone, 2,5-dichlorobenzoquinone, 2,5-dichlorobenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphthoquinone, 2,3-dichloronaphthoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine, or fullerene C60 is preferred, hexacyanobutadiene, hexacyanobenzene, tetracyanoethylene, tetracyanoquinodimethane, tetrafluorotetracyanoquinodimethane, p-fluoranyl, p-chloranyl, p-bromanyl, 2,6-dichlorobenzoquinone, 2,5-dichlorobenzoquinone, 2,3-dichloronaphthoquinone, 1,2,4,5-tetracyanobenzene, 2,3-dichloro-5,6-dicyanobenzoquinone or 2,3,5,6-tetracyanopyridine is more preferred, and tetrafluorotetracyanoquinodimethane is particularly preferred.

These electron-accepting dopants may be used alone or in combination. The electron-accepting dopants is used in a different amount depending on the type of a material, but is used preferably in an amount of 0.01 mass % to 50 mass %, more preferably 0.05 mass % to 20 mass %, and particularly preferably 0.1 mass % to 10 mass % based on the hole transporting layer material.

From the viewpoint of lowering the driving voltage, a thickness of each of the hole injection layer and the hole transporting layer is preferably 500 nm or less.

The thickness of the hole transporting layer is preferably 1 nm to 500 nm, more preferably 5 nm to 200 nm, and even more preferably 10 nm to 100 nm. Also, the thickness of the hole injection layer is preferably 0.1 nm to 200 nm, more preferably 0.5 nm to 100 nm, and even more preferably 1 nm to 100 nm.

Each of the hole injection layer and the hole transporting layer may have a single layer structure composed of one or two or more kinds of the above-described materials, or may have a multilayer structure composed of a plurality of layers of the same or different compositions.

—Electron Injection Layer and Electron Transporting Layer—

The electron injection layer and the electron transporting layer are layers having a function of accepting electrons from the cathode or the cathode side to transport the electron into the anode side.

With respect to the hole injection layer, the hole transporting layer, the electron injection layer and the electron transporting layer, the subject matters described in paragraph Nos. [0165] to [0167] of Japanese Patent Application Laid-Open No. 2008-270736 may be applied to the present invention.

—Hole Blocking Layer—

The hole blocking layer is a layer having a function of preventing holes transported from the anode side to the light emitting layer from passing toward the cathode side. In the present invention, it is possible to provide the hole blocking layer as an organic layer adjacent to the light emitting layer at a cathode side.

Examples of organic compounds forming the hole blocking layer include aluminum complexes such as aluminum (III) bis(2-methyl-8-quinolinato)-4-phenylphenolate (abbreviated as BAlq), triazole derivatives, phenanthroline derivatives such as 2,9-dimethyl-4,7-diphenyl-1,10-phenanthroline (abbreviated as BCP), or the like.

The thickness of the hole blocking layer is preferably 1 nm to 500 nm, more preferably 5 nm to 200 nm, and even more preferably 10 nm to 100 nm.

The hole blocking layer may have a single layer structure composed of one or two or more kinds of the above-described materials, or may have a multilayer structure composed of a plurality of layers of the same or different compositions.

—Electron Blocking Layer—

The electron blocking layer is a layer having a function of preventing electrons transported from the cathode side to the light emitting layer from passing toward the anode side. In the present invention, it is possible to provide the electron blocking layer as an organic layer adjacent to the light emitting layer at a anode side.

As examples of organic compounds forming the electron blocking layer, the above-described materials exemplified as the hole transporting material may be applied.

The thickness of the electron blocking layer is preferably 1 nm to 500 nm, more preferably 5 nm to 200 nm, and even more preferably 10 nm to 100 nm.

The electron blocking layer may have a single layer structure composed of one or two or more kinds of the above-described materials, or may have a multilayer structure composed of a plurality of layers of the same or different compositions.

<Protective Layer>

In the present invention, the whole of the organic EL device may be protected with a protective layer.

With respect to the protective layer, the subject matters described in paragraph No. [0169] to [0170] of Japanese Patent Application Laid-Open No. 2008-270736 may be applied to the present invention.

<Sealing Container>

In the device of the present invention, the whole device may be sealed using a sealing container.

With respect to the sealing container, the subject matters described in paragraph No. [0171] of Japanese Patent Application Laid-Open No. 2008-270736 may be applied to the present invention.

(Driving)

In the organic electroluminescence device of the present invention, light emission may be obtained by applying a DC voltage (typically 2 volts to 15 volts) (which may include an alternating current component if necessary) or a direct current between the anode and the cathode.

With respect to the driving method of the organic electroluminescence device of the present invention, driving methods described in Japanese Patent Application Laid-Open No. Hei 2-148687, Japanese Patent Application Laid-Open No. Hei 6-301355, Japanese Patent Application Laid-Open No. Hei 5-29080, Japanese Patent Application Laid-Open No. Hei 7-134558, Japanese Patent Application Laid-Open No. Hei 8-234685, and Japanese Patent Application Laid-Open No. Hei 8-241047, and Japanese Patent No. 2784615, U.S. Pat. Nos. 5,828,429, and 6,023,308, or the like may be applied.

In the luminescence device of the present invention, it is possible to enhance light extraction efficiency by various known methods. For example, refractive indexes of a substrate, ITO layer and an organic layer are controlled by treating (e.g. forming a fine surface irregularity pattern) the surface shape of the substrate. It is also possible to improve external quantum efficiency through the enhancement of light extraction efficiency, for example, by controlling thicknesses of a substrate, ITO layer and an organic layer.

The external quantum efficiency of the organic electroluminescence device of the present invention is preferably 20% to 30%. As a value of external quantum efficiency, a maximum value of external quantum efficiency when driving the device at 20° C., or a value of external quantum efficiency near 100 to 300 cd/m$^2$ when driving the device at 20° C. may be used.

The luminescence device of the present invention may be in a so-called top emission system of extracting light from the anode side.

The organic EL device of the present invention may have a resonator structure. For example, a multilayer mirror composed of a plurality of laminated films differing in the refractive index, a transparent or semi-transparent electrode, a light emitting layer, and a metal electrode are superposed on a transparent substrate. Light generated in the light emitting layer repeats reflections between the multilayer mirror and the metal electrode and resonates therebetween.

In another preferred embodiment, each of a transparent or semi-transparent electrode and a metal electrode functions as a reflector on a transparent substrate, and light generated in the light emitting layer repeats reflection and resonates therebetween.

In order to form a resonance structure, the effective refractive index of two reflectors and the optical path length determined from the refractive index and thickness of each layer between the reflectors are adjusted to optimal values for obtaining a desired resonance wavelength. The calculation formula in the case of the first embodiment is described in Japanese Patent Application Laid-Open No. Hei 9-180883, and the calculation formula in the case of the second embodiment is described in Japanese Patent Application Laid-Open No. 2004-127795.

(Use of Luminescence Device of the Present Invention)

The luminescence device of the present invention may be suitably used for light emission apparatuses, pixels, display devices, displays, backlights, electrophotography, illumination light sources, recording light sources, exposure light sources, reading light sources, indicators, signboards, interiors, optical communication, or the like. Particularly, the luminescence device of the present invention is preferably used for a device that is driven in a region of high light emission luminance intensity, such as illumination apparatus and display apparatus.

Next, the light emission apparatus of the present invention is described below with reference to FIG. 2.

The light emission apparatus of the present invention uses the above-described organic electroluminescence device.

Figure 2:
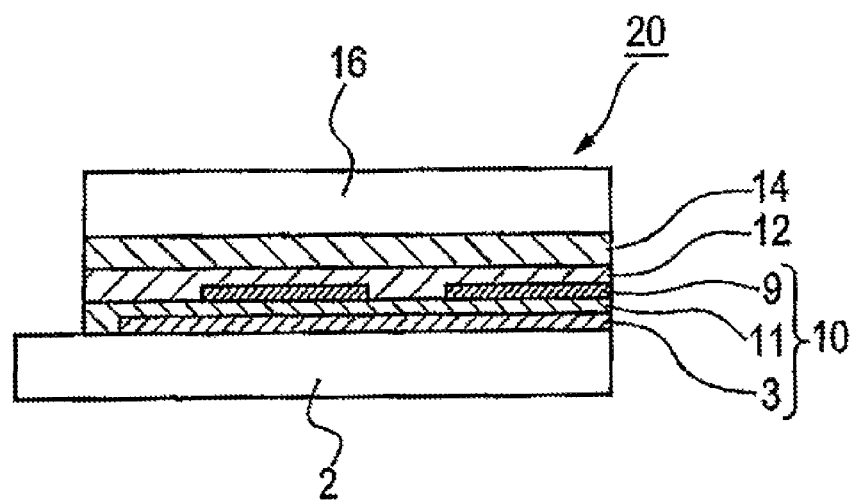
FIG. 2 is a schematic view illustrating an example of a light emitting apparatus according to the present invention (the second embodiment).

FIG. 2 is a sectional view schematically showing one exemplary example of the light emission apparatus of the present invention.

The light emission apparatus 20 of FIG. 2 is composed of a substrate (supporting substrate) 2, an organic electroluminescence device 10, a sealing container 16 and the like.

The organic electroluminescence device 10 is configured by sequentially stacking an anode (first electrode) 3, an organic layer 11 and a cathode (second electrode) 9 on a substrate 2. A protective layer 12 is stacked on the cathode 9, and a sealing container 16 is provided on the protective layer 12 through an adhesion layer 14. Also, a part of electrodes 3 and 9, a partition wall, an insulating layer and the like are omitted.

Herein, as for the adhesion layer 14, a photocurable or thermosetting adhesive such as epoxy resin may be used and, for example, a thermosetting adhesive sheet may also be used.

The light emission apparatus of the present invention is not particularly limited in its application and, for example, may be used not only as an illumination apparatus but also a display apparatus of a television set, a personal computer, a cellular phone, an electronic paper and the like.

Then, the illumination apparatus according to an embodiment of the present invention is described below with reference to FIG. 3.

Figure 3:
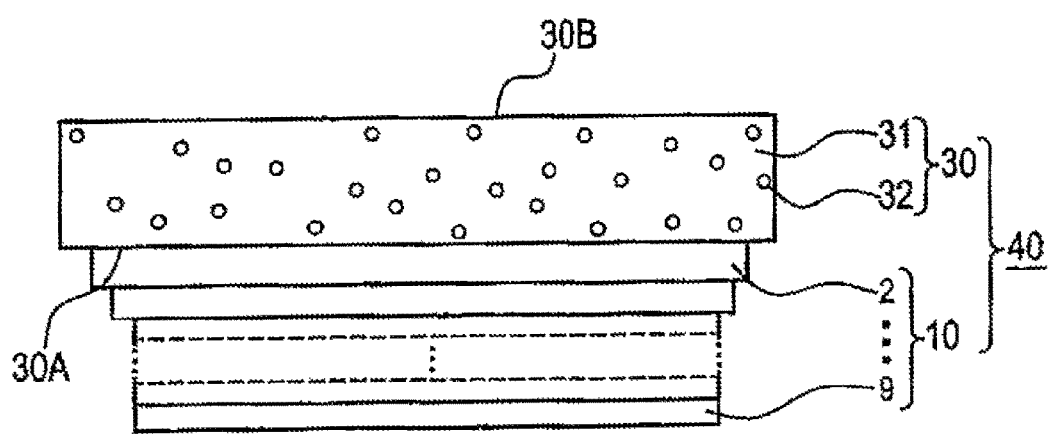
FIG. 3 is a schematic view illustrating an example of an illumination apparatus according to the present invention (the third embodiment).

FIG. 3 is a sectional view schematically showing one exemplary example of the illumination apparatus according to an embodiment of the present invention.

The illumination apparatus 40 according to an embodiment of the present invention includes, as shown in FIG. 3, the above-described organic EL device 10 and a light scattering member 30. More specifically, the illumination apparatus 40 is configured so that the substrate 2 of the organic EL device 10 and the light scattering member 30 are put into contact.

The light scattering member 30 is not particularly limited as long as the member is capable of scattering light, but in FIG. 3, a member obtained by dispersing fine particles 32 in a transparent substrate 31 is used. Suitable examples of the transparent substrate 31 include a glass substrate. Suitable examples of the fine particles 32 include transparent resin fine particles. As the glass substrate and the transparent resin fine particles, known products may be used for both. In such an illumination apparatus 40, when light emitted from the organic electroluminescence device 10 is incident on the light incident surface 30A of the scattering member 30, the incident light is scattered by the light scattering member 30 and the scattered light is output as illuminating light from the light output surface 30B.

EXAMPLE

Hereinafter, the present invention will be described in detail with reference to Examples, but the present invention is not limited thereto.

The compound represented by Formula (BN-1) used in the following Examples was prepared, for example, by a method described in US Patent Application No. 2009/0009065. For example, compound B-1 may be prepared by a method described in [0307] of US Patent Application No. 2009/0009065 using 2-bromo-6-(2-naphthyl)naphthalene and 3-(9-phenanthryl)phenyl borate as starting materials. In addition, the compound represented by Formula (PQ-1) may be prepared by using a method described in US Patent Application No. 2008/0261076. For example, P-1 may be prepared by a method described in [0064] to [0067] of US Patent Application No. 2008/0264076.

Comparative Example 1-1

A glass substrate having an indium tin oxide (ITO) film having a thickness of 0.5 mm and each side of 2.5 cm in square (manufactured by Geomatec Co., Ltd., and surface resistance 10Ω/□ (square)) was put into a washing container, ultrasonically washed in 2-propanol, followed by UV-ozone treatment for 30 minutes. The following organic layers were sequentially vapor deposited on this transparent anode (ITO film) by means of vacuum deposition.

First layer (HIL): HIL-A: film thickness 30 nm
Second layer (HTL): HTL-P: film thickness 20 nm
Third layer (EML): Dopant: RD-1 (5 mass %), host material: B-1 (95 mass %): film thickness 40 nm
Fourth layer: Alq (tris(8-hydroxyquinoline) aluminum complex): film thickness 30 nm Then, 0.2 nm of lithium fluoride and 70 nm of metal aluminum were vapor deposited in this order thereon, thereby forming a cathode.

The resultant laminate was placed in a glove box substituted with argon gas without being in contact with the atmosphere, and sealed using a stainless-made sealing can and a UV-curable adhesive (XNR5516HV, manufactured by Nagase-CHIBA Ltd.) to obtain a comparative device 1-1.

[Evaluation of Performance of Organic Electroluminescence Devices]

The performance of each of the obtained devices was evaluated by measuring the external quantum efficiency, driving voltage, driving durability and driving voltage increment with time while driving at a high temperature. Also, various measurements were performed as follows. The results are shown in the following Table 1.

(a) External Quantum Efficiency

DC voltage was applied to each device by using a Source Measure Unit 2400 manufactured by Toyo Technica Corporation to enable the devices to emit light, and the luminance intensity was measured by using a luminance meter BM-8 manufactured by TOPCON CORPORATION. Emission spectra and emission wavelengths were measured by using a spectrum analyzer PMA-11 manufactured by Hamamatsu Photonics K.K. On the basis of the obtained numerical values, the external quantum efficiency in the vicinity of the luminance intensity of about 1000 cd/m² was calculated by a luminance intensity conversion method.

(b) Driving Voltage

DC voltage was applied to each device so that the luminance intensity was 1000 cd/m², thereby enabling the device to emit light. The voltage applied at that time was defined as an index for evaluating driving voltage.

(c) Driving Durability

DC voltage was applied to each device so that luminance intensity was 1000 cd/m², and then the time until the luminance intensity decreased to 500 cd/m² was measured. The measured time was defined as an index for evaluating driving durability.

(d) Difference in Voltage Increment Depending on Difference in Driving Temperature The difference (V) in voltage increment when each device reaches a luminance intensity of 500 cd/m² after being driven at 25° C.-20° C. under an initial luminance intensity of 1000 cd/m² was used as an index.

Examples 1-1 to 1-25 and Comparative Examples 1-2 to 1-12

Various devices were obtained in the same manner as described in Comparative Example 1-1, except that constituting materials of the third layer and the fourth layer were changed into compositions shown in the following Table 1.

TABLE 1

| Device No. | HIL (30 nm) | HTL (20 nm) | EML (40 nm) Host | EML (40 nm) Dopant | ETL (30 nm) | EQE (%) | Driving Voltage (V) | Driving Durability (H) | Difference in voltage increment (V) |
|---|---|---|---|---|---|---|---|---|---|
| Comparative Device 1-1 | HIL-A | HTL-P | B-1 | RD-1 | Alq | 3.7 | 7.5 | 6400 | 1.7 |
| Comparative Device 1-2 | HIL-A | HTL-P | B-1 | RD-1 | ETL-K | 5.7 | 7.4 | 6500 | 2.5 |
| Comparative Device 1-3 | HIL-A | HTL-P | B-1 | RD-3 | ETL-K | 4.8 | 7.4 | 4900 | 1.8 |
| Comparative Device 1-4 | HIL-A | HTL-P | B-1 | RD-4 | ETL-K | 5.2 | 7.4 | 5700 | 2.0 |
| Comparative Device 1-5 | HIL-A | HTL-P | B-1 | RD-5 | ETL-K | 4.2 | 7.9 | 2500 | 2.3 |
| Comparative Device 1-6 | HIL-A | HTL-P | B-1 | RD-6 | ETL-K | 2.9 | 8.2 | 1800 | 2.5 |
| Comparative Device 1-7 | HIL-A | HTL-P | CBP | P-1 | ETL-K | 6.9 | 7.5 | 9000 | 2.4 |
| Comparative Device 1-8 | HIL-A | HTL-P | BAlq | P-1 | ETL-K | 5.3 | 7.8 | 8000 | 2.6 |
| Comparative Device 1-9 | HIL-A | HTL-P | CBP | P-13 | ETL-K | 6.8 | 7.4 | 7100 | 2.4 |
| Comparative Device 1-10 | HIL-A | HTL-P | BAlq | P-13 | ETL-K | 5.0 | 7.6 | 6500 | 2.6 |
| Comparative Device 1-11 | HIL-A | HTL-P | CBP | RD-1 | ETL-K | 3.4 | 7.6 | 6000 | 3.2 |
| Comparative Device 1-12 | HIL-A | HTL-P | BAlq | RD-1 | ETL-K | 3.3 | 7.7 | 4800 | 3.1 |
| Inventive Device 1-1 | HIL-A | HTL-P | B-1 | P-1 | ETL-K | 11.4 | 7.0 | 24000 | 1.0 |
| Inventive Device 1-2 | HIL-A | HTL-P | B-1 | P-2 | ETL-K | 11.0 | 7.0 | 23000 | 1.0 |
| Inventive Device 1-3 | HIL-A | HTL-P | B-1 | P-3 | ETL-K | 11.1 | 6.9 | 20000 | 0.9 |
| Inventive Device 1-4 | HIL-A | HTL-P | B-1 | P-4 | ETL-K | 10.6 | 6.8 | 21000 | 0.9 |
| Inventive Device 1-5 | HIL-A | HTL-P | B-1 | P-5 | ETL-K | 11.7 | 7.0 | 16000 | 1.0 |
| Inventive Device 1-6 | HIL-A | HTL-P | B-1 | P-6 | ETL-K | 11.0 | 6.9 | 20000 | 1.1 |
| Inventive Device 1-7 | HIL-A | HTL-P | B-1 | P-7 | ETL-K | 11.1 | 7.2 | 18000 | 0.9 |
| Inventive Device 1-8 | HIL-A | HTL-P | B-1 | P-8 | ETL-K | 11.4 | 7.1 | 23000 | 1.0 |
| Inventive Device 1-9 | HIL-A | HTL-P | B-1 | P-9 | ETL-K | 10.2 | 7.1 | 14000 | 0.9 |
| Inventive Device 1-10 | HIL-A | HTL-P | B-1 | P-10 | ETL-K | 10.0 | 7.4 | 15000 | 1.0 |
| Inventive Device 1-11 | HIL-A | HTL-P | B-1 | P-11 | ETL-K | 11.5 | 6.8 | 19000 | 1.0 |
| Inventive Device 1-12 | HIL-A | HTL-P | B-1 | P-13 | ETL-K | 11.3 | 6.9 | 24000 | 0.9 |
| Inventive Device 1-13 | HIL-A | HTL-P | B-1 | P-14 | ETL-K | 11.1 | 6.9 | 22000 | 1.1 |
| Inventive Device 1-14 | HIL-A | HTL-P | B-2 | P-1 | ETL-K | 10.5 | 7.0 | 21000 | 1.0 |
| Inventive Device 1-15 | HIL-A | HTL-P | B-3 | P-1 | ETL-K | 10.0 | 7.2 | 20000 | 0.9 |
| Inventive Device 1-16 | HIL-A | HTL-P | B-4 | P-1 | ETL-K | 11.0 | 7.1 | 19000 | 1.0 |
| Inventive Device 1-17 | HIL-A | HTL-P | B-5 | P-1 | ETL-K | 11.4 | 6.9 | 18000 | 1.1 |
| Inventive Device 1-18 | HIL-A | HTL-P | B-6 | P-1 | ETL-K | 11.3 | 7.0 | 21000 | 0.9 |
| Inventive Device 1-19 | HIL-A | HTL-P | B-8 | P-1 | ETL-K | 11.1 | 6.8 | 20000 | 1.0 |
| Inventive Device 1-20 | HIL-A | HTL-P | B-10 | P-1 | ETL-K | 11.0 | 6.9 | 21000 | 1.1 |
| Inventive Device 1-21 | HIL-A | HTL-P | B-11 | P-1 | ETL-K | 10.4 | 6.9 | 19000 | 1.1 |
| Inventive Device 1-22 | HIL-A | HTL-P | B-15 | P-1 | ETL-K | 10.7 | 7.0 | 21000 | 1.0 |
| Inventive Device 1-23 | HIL-A | HTL-P | B-16 | P-1 | ETL-K | 11.0 | 6.9 | 19000 | 0.9 |
| Inventive Device 1-24 | HIL-A | HTL-P | B-17 | P-1 | ETL-K | 10.8 | 7.1 | 16000 | 0.9 |
| Inventive Device 1-25 | HIL-A | HTL-P | B-20 | P-1 | ETL-K | 10.5 | 7.2 | 18000 | 1.0 |

Comparative Example 2-1

A glass substrate having an indium tin oxide (ITO) film having a thickness of 0.5 mm and each side of 2.5 cm in square (manufactured by Geomatec Co., Ltd., and surface resistance 10Ω/□ (square)) was put into a washing container, ultrasonically washed in 2-propanol, followed by UV-ozone treatment for 30 min. The following organic layers were sequentially vapor deposited on this transparent anode (ITO film) by means of vacuum deposition.

First layer (HIL): HIL-1: film thickness 10 nm
Second layer (HTL): NPD: film thickness 40 nm
Third layer (EML): Dopant: RD-1 (5 mass %), host material: B-1 (95 mass %): film thickness 30 nm
Fourth layer (ETL): Alq (tris(8-hydroxyquinoline) aluminum complex): film thickness 30 nm Then, 0.2 nm of lithium fluoride and 70 nm of metal aluminum were vapor deposited in this order thereon, thereby forming a cathode.

The resultant laminate was placed in a glove box substituted with argon gas without being in contact with the atmosphere, and sealed using a stainless-made sealing can and a UV-curable adhesive (XNR5516HV, manufactured by Nagase-CHIBA Ltd.) to obtain a comparative device 2-1, which, in turn, was evaluated as described with reference to the comparative device 1-1.

Examples 2-1 to 2-21 and Comparative Examples 2-2 to 2-3

Various devices were obtained in the same manner as described in Comparative Example 2-1, except that constituting materials of the third layer were changed into compositions shown in the following Table 2. The concentration of the host material equals to the value calculated by subtracting the dopant concentration from 100%.

electrode, a film was formed from a test compound to a film thickness of 100 nm by vacuum deposition. Further, a film was formed on the thin film from aluminum to a film thickness of 250 nm, thereby forming a counter electrode.

(b) Measurement of thermally stimulated current. The thermally stimulated current of each thin film sample was measured by a thermally stimulated current analyzer, TS-FETT, available from Rigaku Denki Co., Ltd. Each thin film sample was cooled to 93K at a rate of 5 K/min and maintained at this temperature for 20 minutes. Next, light with a $\lambda_{max}$=330 nm (using xenon lamp light passed through a band pass filter) is irradiated to the sample for 5 minutes while maintaining 93K. Then, temperature was increased to 200K at a rate of 10 K/min while applying a bias of 0.5V, and the current flowing at that time was measured. As a result, B-1 and BAlq subjected to sublimation purification

TABLE 2

| Device No. | HIL (10 nm) | HTL (40 nm) | EML (40 nm) Host | Dopant (Conc. %) | ETL (55 nm) | EQE (%) | Driving Voltage (V) | Driving Durability (H) | Difference in voltage increment (V) |
|---|---|---|---|---|---|---|---|---|---|
| Comparative Device 2-1 | HIL-1 | NPD | B-1 | RD-1(5) | Alq | 3.9 | 7.2 | 4800 | 2.0 |
| Comparative Device 2-2 | HIL-1 | NPD | CBP | P-1(5) | Alq | 4.8 | 7.0 | 5200 | 2.1 |
| Comparative Device 2-3 | HIL-1 | NPD | CBP | RD-1(5) | Alq | 3.0 | 7.5 | 4300 | 2.5 |
| Inventive Device 2-1 | HIL-1 | NPD | B-1 | P-1(5) | Alq | 11.2 | 6.3 | 22000 | 1.0 |
| Inventive Device 2-2 | HIL-1 | NPD | B-1 | P-2(5) | Alq | 11.3 | 6.1 | 18000 | 0.9 |
| Inventive Device 2-3 | HIL-1 | NPD | B-1 | P-3(5) | Alq | 10.4 | 6.2 | 17000 | 1.1 |
| Inventive Device 2-4 | HIL-1 | NPD | B-1 | P-4(5) | Alq | 10.6 | 6.6 | 17000 | 0.9 |
| Inventive Device 2-5 | HIL-1 | NPD | B-1 | P-5(5) | Alq | 11.1 | 6.4 | 18000 | 1.1 |
| Inventive Device 2-6 | HIL-1 | NPD | B-1 | P-6(5) | Alq | 11.0 | 6.8 | 19000 | 1.0 |
| Inventive Device 2-7 | HIL-1 | NPD | B-1 | P-7(5) | Alq | 10.7 | 6.5 | 15000 | 0.9 |
| Inventive Device 2-8 | HIL-1 | NPD | B-1 | P-8(5) | Alq | 10.7 | 6.3 | 16000 | 0.9 |
| Inventive Device 2-9 | HIL-1 | NPD | B-1 | P-9(5) | Alq | 11.3 | 6.2 | 15000 | 1.0 |
| Inventive Device 2-10 | HIL-1 | NPD | B-1 | P-11(5) | Alq | 11.0 | 6.4 | 17000 | 0.9 |
| Inventive Device 2-11 | HIL-1 | NPD | B-1 | P-13(5) | Alq | 12.0 | 6.6 | 20000 | 1.3 |
| Inventive Device 2-12 | HIL-1 | NPD | B-1 | P-14(5) | Alq | 11.9 | 6.5 | 18000 | 0.9 |
| Inventive Device 2-13 | HIL-1 | NPD | B-2 | P-1(5) | Alq | 9.9 | 6.4 | 13000 | 1.2 |
| Inventive Device 2-14 | HIL-1 | NPD | B-3 | P-1(5) | Alq | 10.0 | 6.5 | 13000 | 1.2 |
| Inventive Device 2-15 | HIL-1 | NPD | B-4 | P-1(5) | Alq | 10.4 | 6.7 | 14000 | 1.0 |
| Inventive Device 2-16 | HIL-1 | NPD | B-5 | P-1(5) | Alq | 11.1 | 6.5 | 15000 | 0.9 |
| Inventive Device 2-17 | HIL-1 | NPD | B-6 | P-1(5) | Alq | 10.8 | 6.6 | 14000 | 1.0 |
| Inventive Device 2-18 | HIL-1 | NPD | B-8 | P-1(5) | Alq | 10.9 | 6.7 | 12000 | 0.9 |
| Inventive Device 2-19 | HIL-1 | NPD | B-11 | P-1(5) | Alq | 11.6 | 6.9 | 15000 | 1.3 |
| Inventive Device 2-20 | HIL-1 | NPD | B-15 | P-1(5) | Alq | 10.2 | 6.5 | 12000 | 1.1 |
| Inventive Device 2-21 | HIL-1 | NPD | B-1 | P-1(10) | Alq | 13.8 | 6.2 | 22000 | 1.3 |

Example 3-1 and Comparative Example 3-1

For Compound B-1 and BAlq, thin films were fabricated from samples subjected to sublimation purification once and samples subjected to sublimation purification three times, and then thermally stimulated current was measured. Herein, the samples subjected to sublimation purification once are the same as B-1 and BAlq used for the devices described in Table 1 and Table 2.

(a) Fabrication of Thin Film Samples
A substrate of a glass plate on which an ITO film (film thickness 0.2 μm) is formed was washed with isopropyl alcohol and subjected to UV-ozone treatment for 30 minutes, thereby forming a transparent electrode. On the transparent once had a peak current value between 100K and 150K, while B-1 and BAlq subjected to sublimation purification three times had no peak current value between 100K and 150K.

For the inventive device 1-1 and the comparative device 1-6 described in Table 1, the same devices were fabricated using samples of B-1 and BAlq having no peak current value between 100K and 150K, thereby providing a device 3-1 of the present invention and a comparative device 3-1, respectively. In the column of thermally stimulated current shown in Table 3, a sign A and a sign B represent a case having no peak current value and a case having a peak current, between 100K and 150K, respectively.

TABLE 3

| Device No. | EML Host (TSC condition) | EML Dopant (Conc. %) | EQE (%) | Driving voltage (V) | Driving durability (H) | Difference in voltage increment (V) | Thermally stimulated current |
|---|---|---|---|---|---|---|---|
| Inventive Device 1-1 | B-1 | P-1(5) | 11.4 | 7.0 | 24000 | 1.0 | B |
| Inventive Device 3-1 | B-1 | P-1(5) | 11.6 | 7.0 | 32000 | 1 | A |
| Comparative Device 1-6 | Balq | P-1(5) | 5.3 | 7.8 | 8000 | 2.6 | B |
| Comparative Device 3-1 | Balq | P-1(5) | 5.4 | 7.8 | 10000 | 2.5 | A |

Comparative Example 4-1

A glass substrate having an indium tin oxide (ITO) film having a thickness of 0.5 mm and each side of 2.5 cm in square (manufactured by Geomatec Co., Ltd., and surface resistance 10Ω/□ (square)) was put into a washing container, ultrasonically washed in 2-propanol, followed by UV-ozone treatment for 30 min. After carrying out spin coating of aqueous dispersion of poly(ethylenedioxythiophene) and polystyrene sulfonate (Baytron P available from BAYER: solid content 1.3%) on the transparent anode (ITO film), vacuum drying was performed at 150° C. for 2 hours, thereby forming a PEDOT-PSS layer (first layer) with a thickness of 100 nm.

The following organic layers were sequentially vapor deposited on the first layer by means of vacuum deposition.

Second layer (HIL): HIL-A: film thickness 30 nm
Third layer (HTL): HTL-P: film thickness 20 nm
Fourth layer (EML): Dopant: RD-1 (5 mass %), host material: B-1 (95 mass %): film thickness 40 nm
Fifth layer (ETL): Alq (tris(8-hydroxyquinoline) aluminum complex): film thickness 30 nm Then, 0.2 nm of lithium fluoride and 70 nm of metal aluminum were vapor deposited in this order thereon, thereby forming a cathode.

The resultant laminate was placed in a glove box substituted with argon gas without being in contact with the atmosphere, and sealed using a stainless-made sealing can and a UV-curable adhesive (XNR5516HV, manufactured by Nagase-CHIBA Ltd.) to obtain a comparative device 4-1.

Examples 4-1 to 4-25 and Comparative Examples 4-2 to 4-12

Various devices were obtained in the same manner as described in Comparative Example 4-1, except that constituting materials of the fourth layer were changed into compositions shown in the following Table 4.

TABLE 4

| Device No. | HIL (30 nm) | HTL (20 nm) | EML (40 nm) Host | EML (40 nm) Dopant | ETL (30 nm) | EQE (%) | Driving Voltage (V) | Driving Durability (H) | Difference in voltage increment (V) |
|---|---|---|---|---|---|---|---|---|---|
| Comparative Device 4-1 | HIL-A | HTL-P | B-1 | RD-1 | Alq | 2.5 | 7.4 | 2800 | 1.9 |
| Comparative Device 4-2 | HIL-A | HTL-P | B-1 | RD-1 | ETL-K | 2.9 | 7.5 | 2700 | 2.8 |
| Comparative Device 4-3 | HIL-A | HTL-P | B-1 | RD-3 | ETL-K | 3.1 | 7.5 | 1900 | 1.9 |
| Comparative Device 4-4 | HIL-A | HTL-P | B-1 | RD-4 | ETL-K | 2.7 | 7.6 | 2900 | 2.4 |
| Comparative Device 4-5 | HIL-A | HTL-P | B-1 | RD-5 | ETL-K | 2.5 | 8.0 | 1300 | 2.7 |
| Comparative Device 4-6 | HIL-A | HTL-P | B-1 | RD-6 | ETL-K | 1.3 | 8.4 | 1000 | 3.4 |
| Comparative Device 4-7 | HIL-A | HTL-P | CBP | P-1 | ETL-K | 3.4 | 7.5 | 4500 | 2.3 |
| Comparative Device 4-8 | HIL-A | HTL-P | BAlq | P-1 | ETL-K | 2.2 | 7.6 | 4000 | 2.5 |
| Comparative Device 4-9 | HIL-A | HTL-P | CBP | P-13 | ETL-K | 2.9 | 7.3 | 4000 | 2.2 |
| Comparative Device 4-10 | HIL-A | HTL-P | BAlq | P-13 | ETL-K | 2.8 | 7.5 | 3800 | 2.8 |
| Comparative Device 4-11 | HIL-A | HTL-P | CBP | RD-1 | ETL-K | 1.6 | 7.7 | 3200 | 3.1 |
| Comparative Device 4-12 | HIL-A | HTL-P | BAlq | RD-1 | ETL-K | 1.9 | 7.8 | 2400 | 3.0 |
| Inventive Device 4-1 | HIL-A | HTL-P | B-1 | P-1 | ETL-K | 7.0 | 6.9 | 10000 | 1.0 |
| Inventive Device 4-2 | HIL-A | HTL-P | B-1 | P-2 | ETL-K | 6.9 | 6.9 | 11000 | 1.0 |
| Inventive Device 4-3 | HIL-A | HTL-P | B-1 | P-3 | ETL-K | 7.2 | 6.9 | 10000 | 1.0 |
| Inventive Device 4-4 | HIL-A | HTL-P | B-1 | P-4 | ETL-K | 7.4 | 6.8 | 10000 | 0.9 |
| Inventive Device 4-5 | HIL-A | HTL-P | B-1 | P-5 | ETL-K | 7.3 | 7.0 | 9500 | 0.9 |
| Inventive Device 4-6 | HIL-A | HTL-P | B-1 | P-6 | ETL-K | 7.8 | 6.9 | 9600 | 1.1 |
| Inventive Device 4-7 | HIL-A | HTL-P | B-1 | P-7 | ETL-K | 7.7 | 7.1 | 9300 | 1.0 |
| Inventive Device 4-8 | HIL-A | HTL-P | B-1 | P-8 | ETL-K | 7.6 | 7.1 | 14000 | 1.0 |
| Inventive Device 4-9 | HIL-A | HTL-P | B-1 | P-9 | ETL-K | 7.6 | 7.1 | 8000 | 1.1 |
| Inventive Device 4-10 | HIL-A | HTL-P | B-1 | P-10 | ETL-K | 7.5 | 7.2 | 7500 | 1.0 |
| Inventive Device 4-11 | HIL-A | HTL-P | B-1 | P-11 | ETL-K | 7.6 | 7.3 | 9000 | 1.1 |
| Inventive Device 4-12 | HIL-A | HTL-P | B-1 | P-13 | ETL-K | 7.9 | 6.9 | 13000 | 1.0 |
| Inventive Device 4-13 | HIL-A | HTL-P | B-1 | P-14 | ETL-K | 7.4 | 7.5 | 11000 | 1.1 |
| Inventive Device 4-14 | HIL-A | HTL-P | B-2 | P-1 | ETL-K | 6.9 | 6.9 | 10000 | 0.9 |
| Inventive Device 4-15 | HIL-A | HTL-P | B-3 | P-1 | ETL-K | 6.9 | 7.1 | 12000 | 0.9 |
| Inventive Device 4-16 | HIL-A | HTL-P | B-4 | P-1 | ETL-K | 7.0 | 7.1 | 11000 | 1.0 |
| Inventive Device 4-17 | HIL-A | HTL-P | B-5 | P-1 | ETL-K | 7.1 | 7.0 | 8000 | 1.2 |
| Inventive Device 4-18 | HIL-A | HTL-P | B-6 | P-1 | ETL-K | 7.8 | 7.0 | 10000 | 0.9 |
| Inventive Device 4-19 | HIL-A | HTL-P | B-8 | P-1 | ETL-K | 7.5 | 6.8 | 12000 | 1.0 |
| Inventive Device 4-20 | HIL-A | HTL-P | B-10 | P-1 | ETL-K | 7.4 | 6.9 | 8500 | 1.2 |
| Inventive Device 4-21 | HIL-A | HTL-P | B-11 | P-1 | ETL-K | 7.3 | 6.9 | 7600 | 1.1 |
| Inventive Device 4-22 | HIL-A | HTL-P | B-15 | P-1 | ETL-K | 7.7 | 6.9 | 10500 | 1.0 |
| Inventive Device 4-23 | HIL-A | HTL-P | B-16 | P-1 | ETL-K | 7.5 | 6.9 | 9600 | 1.2 |

TABLE 4-continued

| Device No. | HIL (30 nm) | HTL (20 nm) | EML (40 nm) Host | EML (40 nm) Dopant | ETL (30 nm) | EQE (%) | Driving Voltage (V) | Driving Durability (H) | Difference in voltage increment (V) |
|---|---|---|---|---|---|---|---|---|---|
| Inventive Device 4-24 | HIL-A | HTL-P | B-17 | P-1 | ETL-K | 7.2 | 7.1 | 8200 | 0.9 |
| Inventive Device 4-25 | HIL-A | HTL-P | B-20 | P-1 | ETL-K | 7.0 | 7.1 | 10000 | 0.9 |

From the results of Table 1 and Table 2, it can be seen that the device of the present invention using a condensed hydrocarbyl group-containing host material represented by Formula (BN-1) and a specific iridium complex represented by Formula (PQ-1) for a light emitting layer has excellent external quantum efficiency and driving durability, and shows a small difference in voltage increment even at a different driving temperature, as compared to the devices of the Comparative Examples.

In addition, it can be seen from the results of Table 3 that when using a sample in which a compound represented by Formula (BN-1) has no peak current value at 100K to 150K as determined by thermally stimulated current of a thin film formed to a film thickness of 100 nm by vacuum deposition of the compound, durability is significantly improved. When the host material is BAlq, improvement of durability is low.

Further, it can be seen from the results of Table 4 that even when any one layer of organic layers is formed by a coating process, the device of the present invention using a host material represented by Formula (BN-1) and a specific iridium complex represented by Formula (PQ-1) for a light emitting layer has excellent external quantum efficiency and driving durability, and shows a small difference in voltage increment even at a different driving temperature, as compared to the devices of the Comparative Examples.

In addition, the device of the present invention has excellent luminous efficiency or durability even when the device is used in a high temperature environment, such as in-vehicle use, and is suitable for light emission apparatuses, display apparatuses and illumination apparatuses.

Structures of the compounds used in the Examples and the Comparative Example are shown below.

RD-1

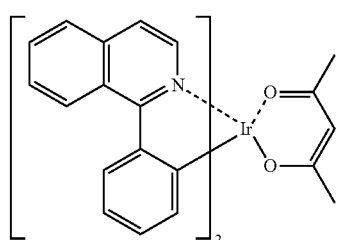

RD-3

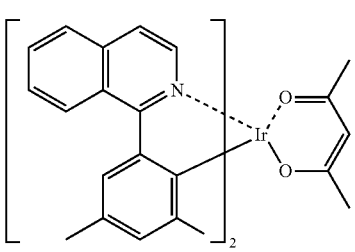

-continued

RD-4

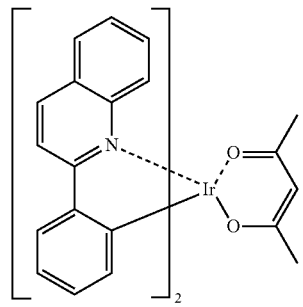

RD-5

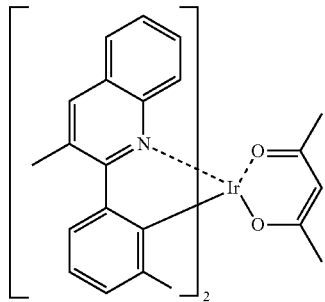

RD-6

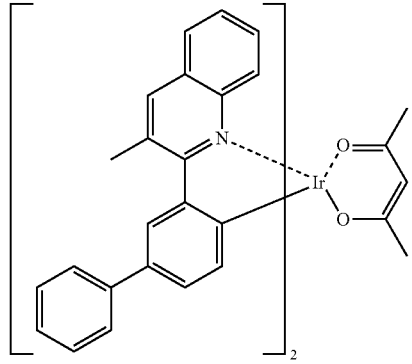

[Chem. 9]

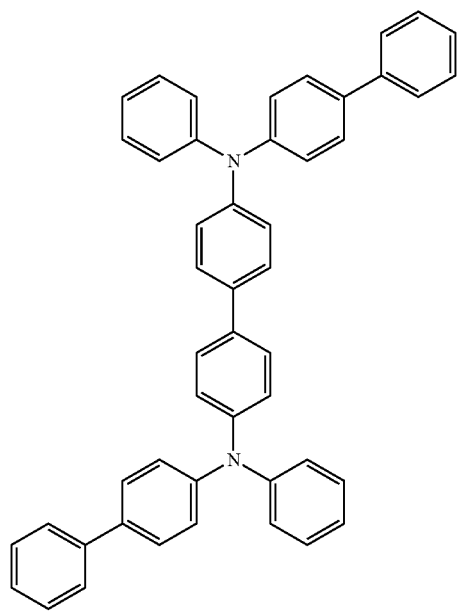

HIL-A

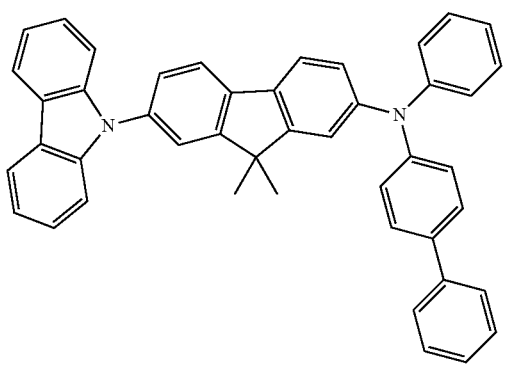

HTL-P

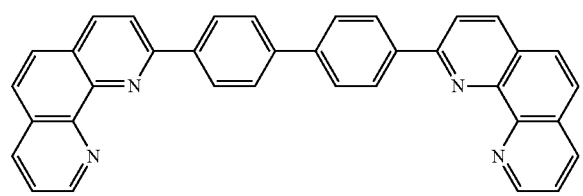

ETL-K

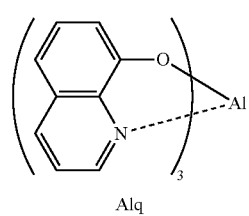

Alq

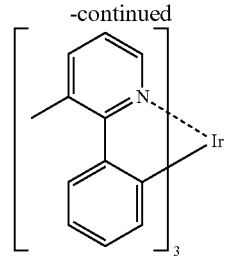

HIL-3

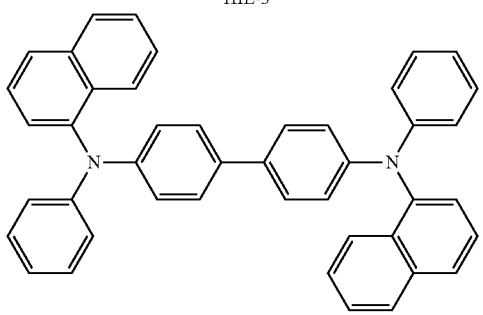

NPD

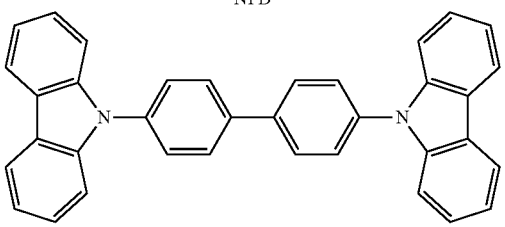

CBP

Abbreviations in Tables are as follows.
HIL: hole injection layer or first layer
HTL: hole transporting layer or second layer
EML: light emitting layer or third layer
ETL: electron transporting layer or fourth layer
EQE: external quantum efficiency

INDUSTRIAL APPLICABILITY

The organic electroluminescence device of the present invention has low electric power consumption and high external quantum efficiency, and shows excellent durability. Moreover, the organic electroluminescence device of the present invention has a small difference in voltage increment even at a different driving temperature, and realizes stable performance for the use of which the driving durability is required in a high temperature environment, such as in-vehicle use.

Although the present invention has been described with reference to detailed and specific embodiments thereof, it is obvious to those skilled in the art that various changes or modifications may be made without departing from the spirit and scope of the present invention.

This application claims priority from Japanese Patent Application (Japanese Patent Application No. 2010-007540) filed on Jan. 15, 2010, the disclosures of which are incorporated herein by reference in its entirety.

EXPLANATION OF REFERENCE NUMERALS AND SYMBOLS

2: Substrate
3: Anode

4: Hole injection layer
5: Hole transporting layer
6: Light emitting layer
7: Hole blocking layer
8: Electron transporting layer
9: Cathode
10: Organic electroluminescence device (organic EL device)
11: Organic layer
12: Protective layer
14: Adhesive layer
16: Sealing container
20: Light emission apparatus
30: Light scattering member
30A: Light incident surface
30B: Light reflecting surface
31: Transparent substrate
32: Fine particles
40: Illumination apparatus

The invention claimed is:

1. A light emitting organic thin film comprising at least one compound represented by Formula (PQ-1) and at least one compound represented by Formula (BN-1):

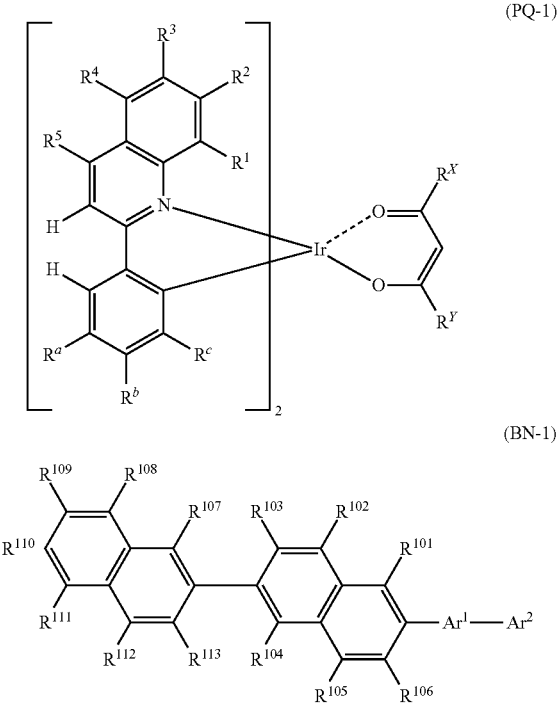

(PQ-1)

(BN-1)

wherein, in Formula (PQ-1), each of $R^a$, $R^b$ and $R^c$ independently represents a hydrogen atom or an alkyl group, any one of $R^a$, $R^b$ and $R^c$ represents a hydrogen atom and the remaining two represent an alkyl group, each of $R^1$ to $R^5$ independently represents a hydrogen atom, an alkyl group, a phenyl group, a fluorine atom or a cyano group, and each of $R^x$ and $R^y$ represents a methyl group;

in Formula (BN-1), $Ar^1$ represents an arylene group that may have a substituent Z, $Ar^2$ represents a tetracenyl group that may have a substituent Z, each of $R^{101}$ to $R^{113}$ represents a hydrogen atom, an alkyl group, a cycloalkyl group, or a phenyl group that may have a substituent Z;

the substituent Z represents an alkyl group, an alkenyl group, an aryl group, an aromatic heterocyclic group, an alkoxy group, an aryloxy group, a fluorine atom, a silyl group, an amino group, a cyano group or a combination thereof.

2. The light emitting organic thin film according to claim 1,
wherein, in Formula (PQ-1), two of $R^a$, $R^b$ and $R^c$ represent a methyl group and the remaining one represents a hydrogen atom.

3. The light emitting organic thin film according to claim 2,
wherein, in Formula (PQ-1), $R^1$ to $R^5$ represent a hydrogen atom.

4. The light emitting organic thin film according to claim 1,
wherein, in Formula (PQ-1), $R^a$ and $R^c$ represent an alkyl group and $R^b$ represents a hydrogen group.

5. The light emitting organic thin film according to claim 4,
wherein, in Formula (PQ-1), $R^1$ to $R^5$ represent a hydrogen atom.

6. The light emitting organic thin film according to claim 1,
wherein, in Formula (BN-1), $R^{102}$, $R^{105}$, $R^{108}$, $R^{109}$, $R^{110}$, $R^{111}$ and $R^{112}$ represent a hydrogen atom.

7. The light emitting organic thin film according to claim 1,
wherein, in Formula (PQ-1), $R^a$ and $R^c$ represent an alkyl group and $R^b$ represents a hydrogen group, and in Formula (BN-1), $R^{102}$ and $R^{105}$ represent a hydrogen atom.

8. A composition comprising the compound represented by Formula (PQ-1) and the compound represented by Formula (BN-1):

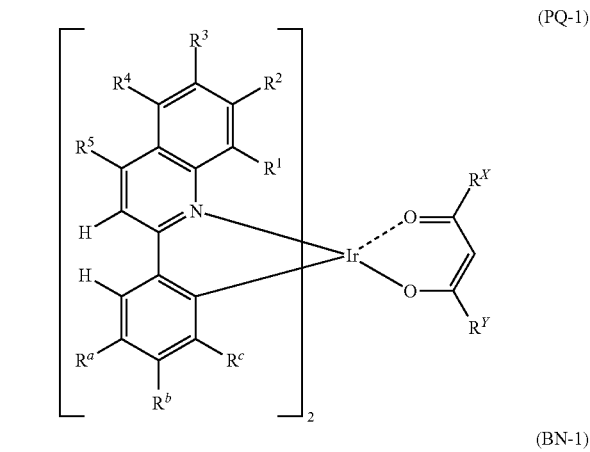

(PQ-1)

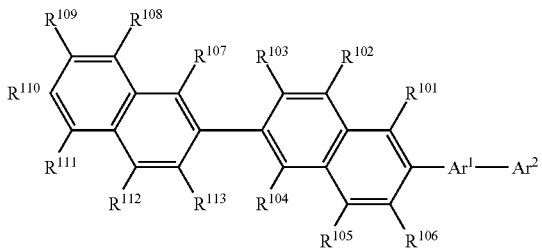

(BN-1)

wherein, in Formula (PQ-1), each of $R^a$, $R^b$ and $R^c$ independently represents a hydrogen atom or an alkyl group, any one of $R^a$, $R^b$ and $R^c$ represents a hydrogen atom and the remaining two represent an alkyl group, each of $R^1$ to $R^5$ independently represents a hydrogen atom, an alkyl group, a phenyl group, a fluorine atom or a cyano group, and each of $R^x$ and $R^y$ represents a methyl group;

in Formula (BN-1), $Ar^1$ represents an arylene group that may have a substituent Z, $Ar^2$ represents a tetracenyl group that may have a substituent Z, each of $R^{101}$ to $R^{113}$ represents a hydrogen atom, an alkyl group, a cycloalkyl group, or a phenyl group that may have a substituent Z; and the substituent Z represents an alkyl group, an alkenyl group, an aryl group, an aromatic heterocyclic group, an alkoxy group, an aryloxy group, a fluorine atom, a silyl group, an amino group, a cyano group or a combination thereof.

9. An organic electroluminescence device comprising a pair of electrodes, and an organic layer including a light emitting layer disposed between the electrodes, on a substrate, wherein the light emitting layer comprises at least one compound represented by Formula (PQ-1) and at least one compound represented by Formula (BN-1):

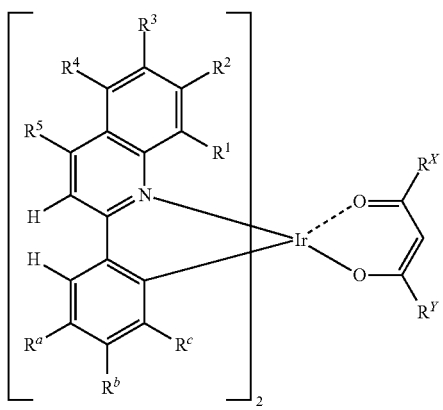

(PQ-1)

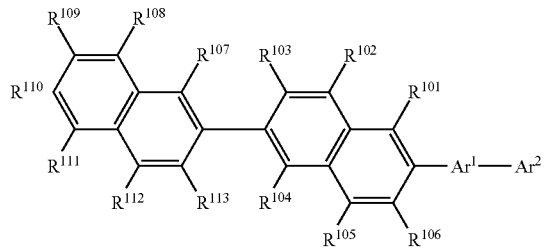

(BN-1)

wherein, in Formula (PQ-1), each of $R^a$, $R^b$ and $R^c$ independently represents a hydrogen atom or an alkyl group, any one of $R^a$, $R^b$ and $R^c$ represents a hydrogen atom and the remaining two represent an alkyl group, each of $R^1$ to $R^5$ independently represents a hydrogen atom, an alkyl group, a phenyl group, a fluorine atom or a cyano group, and each of $R^x$ and $R^y$ represents a methyl group;

in Formula (BN-1), $Ar^1$ represents an arylene group that may have a substituent Z, $Ar^2$ represents a tetracenyl group that may have a substituent Z, each of $R^{101}$ to $R^{113}$ represents a hydrogen atom, an alkyl group, a cycloalkyl group, or a phenyl group that may have a substituent Z; and the substituent Z represents an alkyl group, an alkenyl group, an aryl group, an aromatic heterocyclic group, an alkoxy group, an aryloxy group, a fluorine atom, a silyl group, an amino group, a cyano group or a combination thereof.

10. The organic electroluminescence device according to claim 9
wherein the compound represented by Formula (BN-1) has no peak current value at 100 K to 150 K as determined by thermally stimulated current of a thin film formed to a film thickness of 100 nm by vacuum deposition of the compound.

11. The organic electroluminescence device according to claim 9,
wherein at least one layer of the organic layer is formed by a coating process using a solution or dispersion.

12. A display apparatus using the organic electroluminescence device according to claim 9.

13. An illumination apparatus using the organic electroluminescence device according to claim 9.

* * * * *